US010551365B2

(12) United States Patent
Park et al.

(10) Patent No.: US 10,551,365 B2
(45) Date of Patent: Feb. 4, 2020

(54) PROBE DEVICE FOR ANALYZING PHYSICAL PROPERTIES OF FOOD, HAVING TEETH FORM

(71) Applicant: KOREA FOOD RESEARCH INSTITUTE, Gyeonggi-Do (KR)

(72) Inventors: Dong June Park, Seongnam-si (KR); Dong Man Kim, Gwacheon-si (KR); Chang Ho Lee, Yongin-si (KR); Yong Gi Chun, Yongin-si (KR); Ah Ra Cho, Wonju-si (KR); Kook Nam Pyun, Guri-si (KR)

(73) Assignee: KOREA FOOD RESEARCH INSTITUTE, Gyeonggi-Do (KR)

( * ) Notice: Subject to any disclaimer, the term of this patent is extended or adjusted under 35 U.S.C. 154(b) by 73 days.

(21) Appl. No.: 15/899,023

(22) Filed: Feb. 19, 2018

(65) Prior Publication Data

US 2018/0188223 A1    Jul. 5, 2018

Related U.S. Application Data

(63) Continuation of application No. 15/109,564, filed as application No. PCT/KR2014/009434 on Oct. 7, 2017, now Pat. No. 10,126,281.

(30) Foreign Application Priority Data

Jan. 3, 2014 (KR) .................. 10-2014-0000902
Jun. 2, 2014 (KR) .................. 10-2014-0067234
Jun. 2, 2014 (KR) .................. 10-2014-0067235

(51) Int. Cl.
*G01N 33/02* (2006.01)
*A61C 11/00* (2006.01)
*A61C 11/02* (2006.01)

(52) U.S. Cl.
CPC .............. *G01N 33/02* (2013.01); *A61C 11/00* (2013.01); *A61C 11/025* (2013.01); *A61C 11/02* (2013.01)

(58) Field of Classification Search
CPC .......... G01N 33/025; G01N 2033/105; G01N 33/143; G01N 33/146; G01N 33/02–15;
(Continued)

(56) References Cited

U.S. PATENT DOCUMENTS 1,669,336 A * 5/1928 Highkin ................. A61C 11/02
433/60
2,617,195 A * 11/1952 Perkell ................... A61C 11/02
433/65
(Continued)

FOREIGN PATENT DOCUMENTS

JP      H0624854 Y2    6/1994
JP      2000107207 A   4/2000
(Continued)

*Primary Examiner* — Robert R Raevis
(74) *Attorney, Agent, or Firm* — Victoria C. Cook; Yakov Sidorin; Quarles & Brady LLP

(57) ABSTRACT

The present invention relates to a probe device for analyzing physical properties of food, having a teeth form, and more specifically, to a probe device for analyzing physical properties of food, having a teeth form, capable of objectively analyzing various physical properties felt by a person when chewing food, selecting and using a probe corresponding to a molar, a front tooth or a canine tooth, allowing a vertical motion of a press to be interlocked with a motion of the jaw joint, and allowing chewing experiments similar to real chewing of the human body to be carried out by enabling smooth occlusion of the upper jaw and the lower jaw.

20 Claims, 19 Drawing Sheets

(58) Field of Classification Search
CPC ....... A61C 11/00; A61C 11/025; A61C 11/02; G09B 23/32
USPC .... 73/7, 78, 87, 862.041, 862.042, 862.541, 73/865.6, 432.1, 866; 433/229; 434/263, 434/264; 426/231
See application file for complete search history.

(56) References Cited

U.S. PATENT DOCUMENTS

| | | | |
|---|---|---|---|
| 4,504,226 A | | 3/1985 | Gordon |
| 4,619,611 A | * | 10/1986 | Shimbashi ............. A61C 11/02 433/54 |
| 5,106,296 A | * | 4/1992 | Varde ................. A61C 13/0027 433/54 |
| 5,366,373 A | * | 11/1994 | Mumolo ............. A61C 11/022 433/58 |
| 5,743,732 A | * | 4/1998 | Watson ................. A61C 19/04 433/55 |
| 2008/0261169 A1 | * | 10/2008 | Gutman ................. A61C 11/00 433/69 |

FOREIGN PATENT DOCUMENTS

| | | |
|---|---|---|
| JP | 2004012242 A | 1/2004 |
| JP | 2010539504 A | 12/2010 |

* cited by examiner

PROBE DEVICE FOR ANALYZING PHYSICAL PROPERTIES OF FOOD, HAVING TEETH FORM

CROSS-REFERENCE TO RELATED APPLICATIONS

This application is a divisional of U.S. patent application Ser. No. 15/109,564 filed on Jul. 1, 2016, which represents the national stage entry of PCT International Application No. PCT/KR2014/009434 filed on Oct. 7, 2014 and is based upon and claims the benefit of priority from Korean Patent Application No. 10-2014-0000902, filed on Jan. 3, 2014, Korean Patent Application No. 10-2014-0067234, filed on Jun. 2, 2014 and Korean Patent Application No.10-2014-0067235, filed on Jun. 2, 2014, the entire contents of all of which are incorporated herein by reference.

The present invention relates to a probe device for analyzing physical properties of food, having a teeth form, and more specifically, to a probe device for analyzing physical properties of food, having a teeth form, capable of objectively analyzing various physical properties felt by a person when chewing food, selecting and using a probe corresponding to a molar, a front tooth or a canine tooth, allowing a vertical motion of a press to be interlocked with a motion of the jaw joint, and allowing chewing experiments similar to a real chewing motion of the human body to be carried out by enabling smooth occlusion of the upper jaw and the lower jaw.

BACKGROUND ART

In many cases, deliciousness of food is directly related with feeling felt by the tongue or mouthfeel felt when chewing food, as well as taste of food. Further, a person may also evaluate quality of food by knowing hardness, softness, viscosity, elasticity, density, a size of particles, and the like of food through physical stimulus or mouthfeel in the mouth, and based thereon, determining freshness, maturement, degree of boiling, presence or absence of foreign material, component composition, and the like.

Texture of food greatly affects decision on intake of the food and affects purchase intention of food of a consumer. Therefore, in food industries, texture analysis is performed in product development process so that the food has texture consumers prefer.

The texture analysis of food may be performed by two methods of sensory evaluation and a method using a device. However, in a case of sensory evaluation, it is difficult to objectively digitize texture evaluation items. Accordingly, physical properties of general food are analyzed using various kinds of texture analyzers.

Japanese Patent Laid-Open Publication No. 2006-227021 (published on Aug. 31, 2006) as the related art discloses a porous food palatability evaluation method and a porous food data processing device. The porous food palatability evaluation method and the porous food data processing device are to evaluate palatability of porous food by using values obtained by performing acoustic analysis on sound and vibration generated when crushing and chewing the porous food by using sharpness and roughness as an acoustic measure, without performing a sensory experiment.

Japanese Patent Laid-Open Publication No. 2004-12242 (published on Jan. 15, 2004) discloses a food texture measuring method and a food texture measuring device. The food texture measuring device which quantifies food texture from a position of crushing by measuring vibration at the time of crushing food by bone conduction, includes a plurality of thin plates corresponding to teeth, a first supporter corresponding to the jawbone and having two sensors connected to both sides of the thin plates, a driving unit moving the first supporter to hold the food using the plurality of thin plates and crush the food, a acquisition unit acquiring an electrical signal by converting the vibration at the time of crushing food into an electrical signal by the sensor, and a calculation unit requiring index indicating time difference of the electrical signal, difference in relative amplitude by attenuation, the position of crushing, and a degree of localization.

The analysis using the device like the food texture measuring device according to the related art described above may be easily and rapidly performed, and a result having reproducibility may be obtained. However, since a probe used in such analysis generally has a simple cylinder form, a pin form, a conical form, or a blade form and a thin plate corresponding to teeth as described above is used, food texture by a molar, a front tooth or a canine tooth actually constituting the teeth may not be accurately and objectively analyzed. That is, the probes having simple forms that are currently used have a form and a size completely different from those of teeth of human, thus physical properties of food to be chewed by human may not be objectively analyzed.

Meanwhile, the problem was some what solved by providing a probe device for analyzing physical properties of food, having a standard teeth form of the real human body. That is, the physical properties of food was able to be objectively analyzed using a probe device having a teeth form.

However, since such probe device for analyzing physical properties of food, having a teeth form was configured to move an upper jaw model and a lower jaw model in a vertical direction to be occluded, there is much difference with a real chewing motion of the human body using the jaw joint, therefore, it is difficult to accurately measure the physical properties of food.

DISCLOSURE

Technical Problem

An object of the present invention is to provide probes having a standard teeth form of the real human body, thereby providing a probe device using the probes and being capable of objectively analyzing physical properties of food.

Another object of the present invention is to provide a means for selecting and using all or only a probe having a required tooth form among probes corresponding to respective teeth.

Another object of the present invention is to provide a probe device capable of more accurately and objectively analyzing physical properties of food by allowing a vertical motion of a press to be smoothly interlocked with a chewing motion of an upper jaw model and a lower jaw model to thereby allow a chewing motion similar to a real chewing motion of the jaw joint of the human body to be carried out.

Further, objects of the present invention are not limited to the above-mentioned object. Other objects that are not mentioned may be obviously understood by those skilled in the art to which the present invention pertains from the following description.

Technical Solution

According to an exemplary embodiment of the present invention, there is provided a probe device for analyzing physical properties of food, including: an upper jaw model part formed in a shape of the upper jaw of the human body and including an upper jaw gum part in which upper jaw installation holes for installing respective upper jaw tooth models are each formed; and a lower jaw model part formed to be occluded with the upper jaw model part and including a lower jaw gum part in which lower jaw installation holes for installing respective lower jaw tooth models are each formed, in which probes having an upper jaw teeth form, of which a form and the number are the same as those of molars, canine teeth, and front teeth, are detachably coupled to the upper jaw installation holes, respectively, probes having a lower jaw teeth form, of which a form and the number are the same as those of molars, canine teeth, and front teeth, are detachably coupled to the lower jaw installation holes, respectively, and all of the probes having an upper jaw teeth form and the probes having a lower jaw teeth form are installed in the upper jaw gum part and the lower jaw gum part and used, or only selected probes having a teeth form among the probes having an upper jaw teeth form and the probes having a lower jaw teeth form are installed in the upper jaw gum part and the lower jaw gum part and used.

The probes having an upper jaw teeth form and the probes having a lower jaw teeth form may include contact parts contacting each other; and coupling screw parts coupled to the upper jaw gum part and the lower jaw gum part, respectively, and the coupling screw parts may be coupled to the upper jaw installation holes and the lower jaw installation holes, respectively.

The upper jaw model part may include an upper jaw support member coupled to a lifting member installed in a device for analyzing physical properties of food and ascending and descending; and an upper jaw connection member formed in the same shape as an upper surface area of the upper jaw gum part, disposed between the upper jaw support member and the upper jaw gum part, and having a ring shape for forming an upper jaw space between the upper jaw support member and the upper jaw gum part when the upper jaw support member and the upper jaw gum part are coupled to each other, and the lower jaw model part may include support blocks installed on a table of the device for analyzing physical properties of food and installed to be positioned directly under the upper jaw support member; the lower jaw support member coupled to an upper surface of the support block; and a lower jaw connection member formed in the same shape as a bottom surface area of the lower jaw gum part, disposed between the lower jaw support member and the lower jaw gum part, and having a ring shape for forming a lower jaw space between the lower jaw support member and the lower jaw gum part when the lower jaw support member and the lower jaw gum part are coupled to each other.

The upper jaw model part may include an upper jaw fixing unit for fixing respective coupling screw parts inserted into the upper jaw installation holes, the upper jaw fixing unit may include upper jaw fixing bolts including bolt holes to be fastened to the coupling screw parts in the upper jaw space for detachably fixing the probes having an upper jaw teeth form to the upper jaw gum part, the lower jaw model part may include a lower jaw fixing unit for detachably fixing each coupling screw part inserted into the lower jaw installation hole, and the lower jaw fixing unit may include lower jaw fixing bolts including bolt holes to be fastened to the coupling screw parts in the lower jaw space for fixing the probes having a lower jaw teeth form to the lower jaw gum part.

According to another exemplary embodiment of the present invention, there is provided a probe device for analyzing physical properties of food, including: an upper jaw installation part including an upper jaw model in which respective upper jaw tooth models are installed, and coupled to a pressurizing member of a press device that vertically reciprocates; a lower jaw installation part including a lower jaw model in which lower jaw tooth models are installed, and coupled to the upper jaw installation part by a shaft coupling part so that the lower jaw model is occluded with the upper jaw model; a base on which the lower jaw installation part is installed and supported; and a connection part disposed between the pressurizing member and the upper jaw installation part and allowing the upper jaw installation part and the lower jaw installation part to perform a chewing motion by interlocking of the pressurizing member and the shaft coupling part.

The connection part may include a lower bearing part coupled to the upper jaw installation part; an upper bearing part coupled to the pressurizing member; and a connection rod having both ends each coupled to the upper bearing part and the lower bearing part so as to be freely bent within a predetermined angle range.

The lower bearing part may include a first bearing housing having a first bearing seating step on which a first bearing is seated and a first cover seating step on which a hollowed first bearing cover is seated that are formed therein, and coupled to an upper surface of the upper jaw installation part; and a first shaft joint coupled with a first coupling bolt that is inserted from a bottom surface of the first bearing housing in a state in which one end of the first shaft joint is inserted into the first bearing cover to be integrated with the first bearing housing while rotation of the first shaft joint itself is supported by the first bearing, and having a first joint formed at the other end of the first shaft joint and including a shaft hole for shaft-coupling the first joint to a lower end portion of the connection rod, and the upper bearing part may include a second bearing housing having a second bearing seating step on which a second bearing is seated and a second cover seating step on which a hollowed second bearing cover is seated that are formed therein, and coupled to a bottom surface of the pressurizing member; and a second shaft joint coupled with a second coupling bolt that is inserted from an upper surface of the second bearing housing in a state in which one end of the second shaft joint is inserted into the second bearing cover to be integrated with the second bearing housing while rotation of the second shaft joint itself is supported by the second bearing, and having a second joint formed at the other end of the second shaft joint and including a shaft hole for shaft-coupling the second joint to an upper end portion of the connection rod.

In both end portions of the connection rod, yoke parts to which the first joint and the second joint are inserted, respectively, and rotatably coupled using the shaft may be formed, and joint bearings may be each installed between the shaft hole and the shaft to support bending rotation of the first shaft joint and the second shaft joint.

The shaft coupling part may include a lower connection member having one end coupled to a rear surface of the lower jaw installation part; an upper connection member having one end coupled to a rear surface of the upper jaw installation part; and a connection shaft shaft-coupling the upper connection member and the lower connection member by penetrating through each of the other ends of the upper connection member and the lower connection member.

The base may include a central block on which the lower jaw installation part is seated and coupled; and side blocks each coupled to both sides of the central block to support the central block.

The base may be provided with an angle adjusting unit for adjusting the central block to which the lower jaw installation part is coupled within a predetermined angle based on a horizontal line, and the angle adjusting unit may include a plurality of angle adjusting grooves formed at one side surface or both side surfaces of the central block to which the side blocks are coupled; and angle adjusting protrusions selectively inserted into the angle adjusting grooves and formed at the side block in a position corresponding to the angle adjusting grooves to fix an angle of the central block.

The angle adjusting grooves may be radially disposed based on a fastening hole to which a coupling bolt for coupling the side block to the central block is fastened, and disposed each at both sides of the fastening hole, and the angle adjusting protrusions may be each disposed at both sides thereof based on a bolt through hole through which the coupling bolt penetrates.

In the side blocks, long holes for sliding the central block forward or backward when the pressurizing member is operated to make the connection part operate the upper jaw installation part so that the chewing motion of the upper jaw model and the lower jaw model is performed may be each formed in a vertical direction, and long bolts for coupling the side blocks to a bottom plate of the probe device may penetrate through the long holes to be installed.

In the side blocks, long holes for changing a position of the central block toward a front side or a rear side and fixing the changed position may be each formed in a vertical direction, position determining grooves may be successively formed in the long holes, and long bolts for coupling the side blocks to a bottom plate of the probe device may penetrate through the long holes to be installed.

The connection part may include a lower ball head part coupled to the upper jaw installation part; an upper ball head part coupled to the pressurizing member; and a connection rod having both ends each coupled to the upper ball head part and the lower ball head part so as to be freely bent within a predetermined angle range.

The connection rod may have an upper end portion and a lower end portion to which a first joint ball and a second joint ball are each coupled, the upper ball head part may include a first ball housing cap of which a lower portion is opened to accommodate a first ball housing in which the first joint ball is seated and an edge of an upper end is provided with a flange; a first ball housing cover including a first tension washer seated on the flange and having a first joint ball bushing supporting the first joint ball and installed in the first ball housing cover; and an upper fixing bracket coupled to an upper surface of the first ball housing cover and having an upper surface coupled to the pressurizing member, and the lower ball head part may include a second ball housing cap of which an upper portion is opened to accommodate a second ball housing in which the second joint ball is seated and an edge of a lower end is provided with a flange; and a second ball housing cover including a second tension washer seated on the flange, having a second joint ball bushing supporting the second joint ball and installed in the second ball housing cover, and coupled to an upper surface of the upper jaw installation part.

Advantageous Effects

According to the present invention, there may be provided a probe device for analyzing physical properties of food, having a teeth form that is capable of more objectively and accurately measuring the physical properties of food when analyzing the physical properties of food by using the probe device having a teeth form, as compared to data obtained by analysis using the general probes according to the related art.

Further, a solution for measuring and improving texture of food may be provided by applying a technology for controlling physical properties such as food texture, hardness, and viscosity that are required for each disease of the elderly when analyzing physical properties related to chewing of food by using the device for analyzing physical properties of food to which the probe device having a teeth form is applied.

Further, the probe device having a teeth form, of which a form and the number are the same as those of teeth of the human body is applied, such that an effect of analyzing texture by selectively attaching or detaching the probes having a tooth form that corresponds to a front tooth, a canine tooth, or a molar of the upper jaw and the lower jaw, and analyzing a cutting effect of a front tooth, a rupture effect of a canine tooth, and a trituration effect by a chewing motion of a molar, respectively, may be provided.

Further, an effect of more accurately measuring and objectively analyzing physical properties of food may be provided by allowing the vertical motion of the press device to be smoothly interlocked with the chewing motion of the upper jaw model and the lower jaw model by the connection part having a bearing structure or a ball head structure.

BEST MODE

Hereinafter, preferred exemplary embodiments of the present invention will be described in detail with reference to the accompanying drawings as follows. However, in describing the present invention, a description of a well-known function or configuration will be omitted in order to make the gist of the present invention obvious.

(Examplary Embodiment 1)

Figure 1:
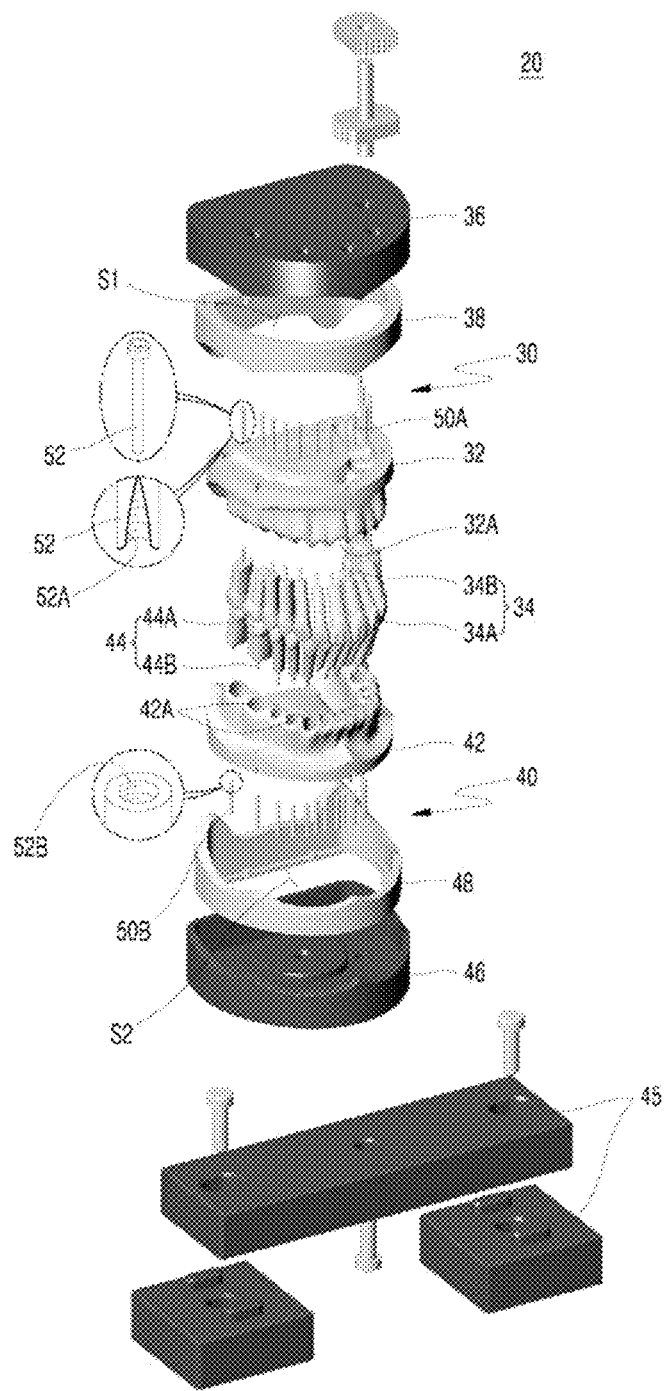
FIG. 1 is an exploded perspective view illustrating a probe device for analyzing physical properties of food according to a first exemplary embodiment of the present invention.
Figure 2:
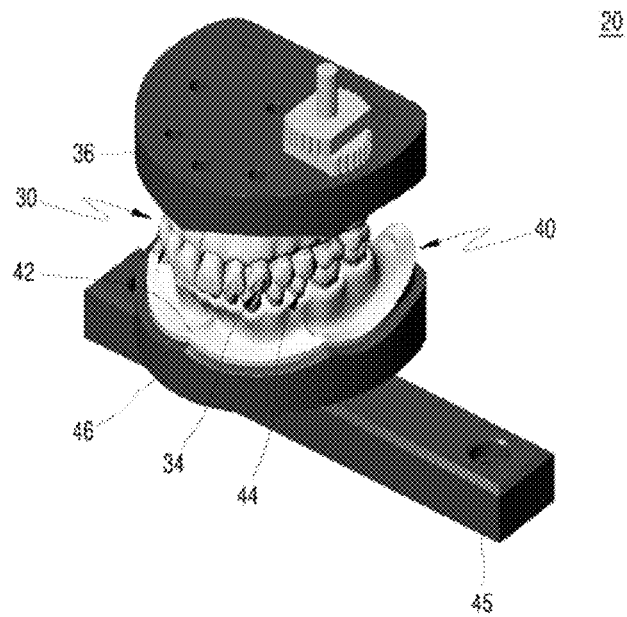
FIG. 2 is a perspective view illustrating an assembled state of the probe device for analyzing physical properties of food illustrated in FIG. 1.
Figure 3:
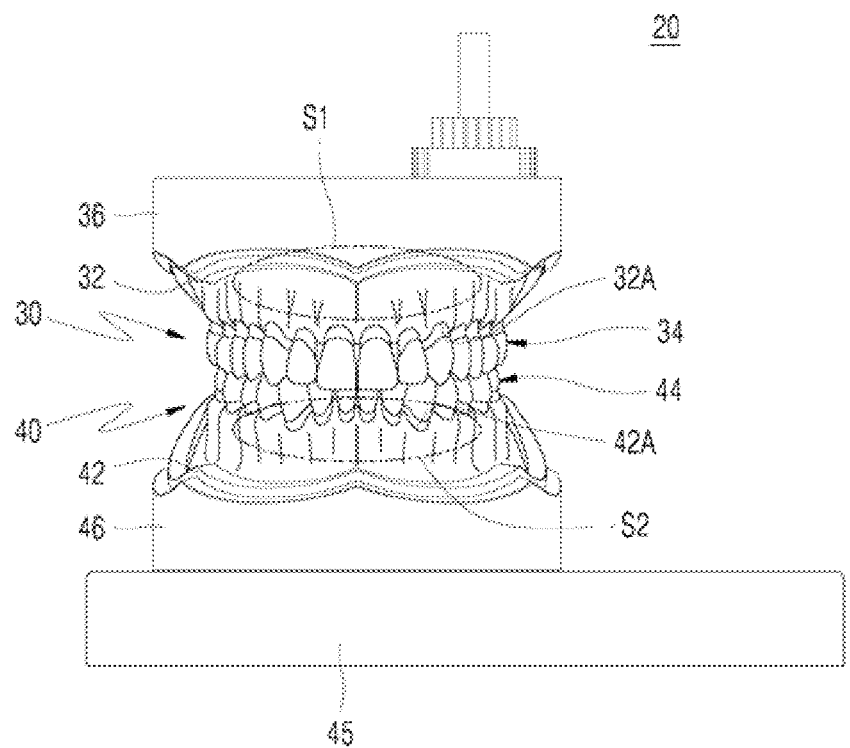
FIG. 3 is a front view illustrating the probe device for analyzing physical properties of food illustrated in FIG. 1.
Figure 4:
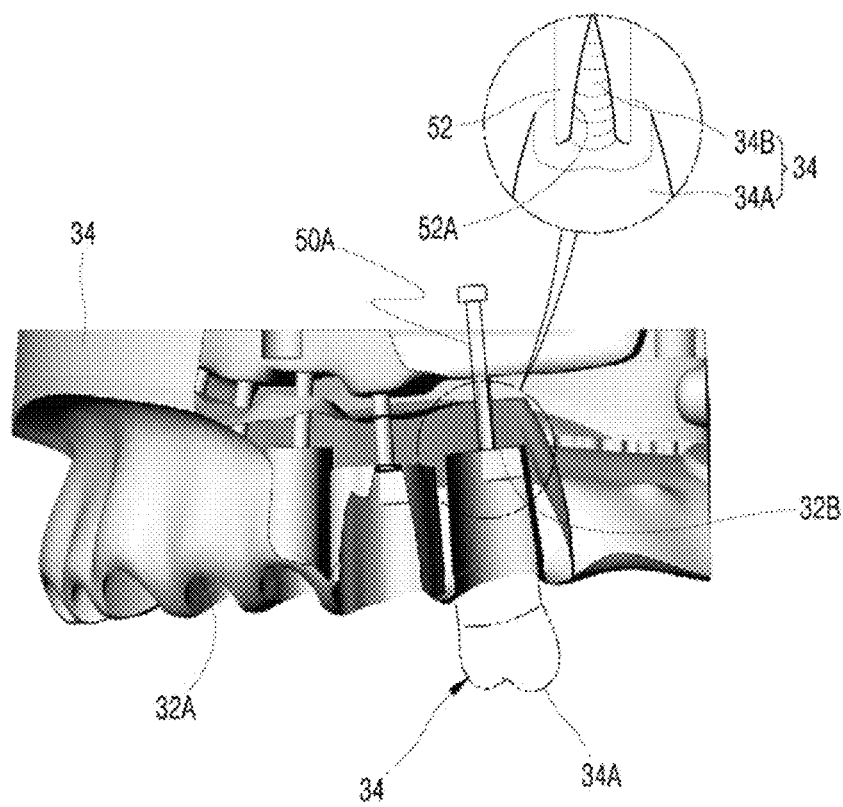
FIG. 4 is a partially enlarged cross-sectional view illustrating an upper jaw fixing unit illustrated in FIG. 1.
Figure 5:
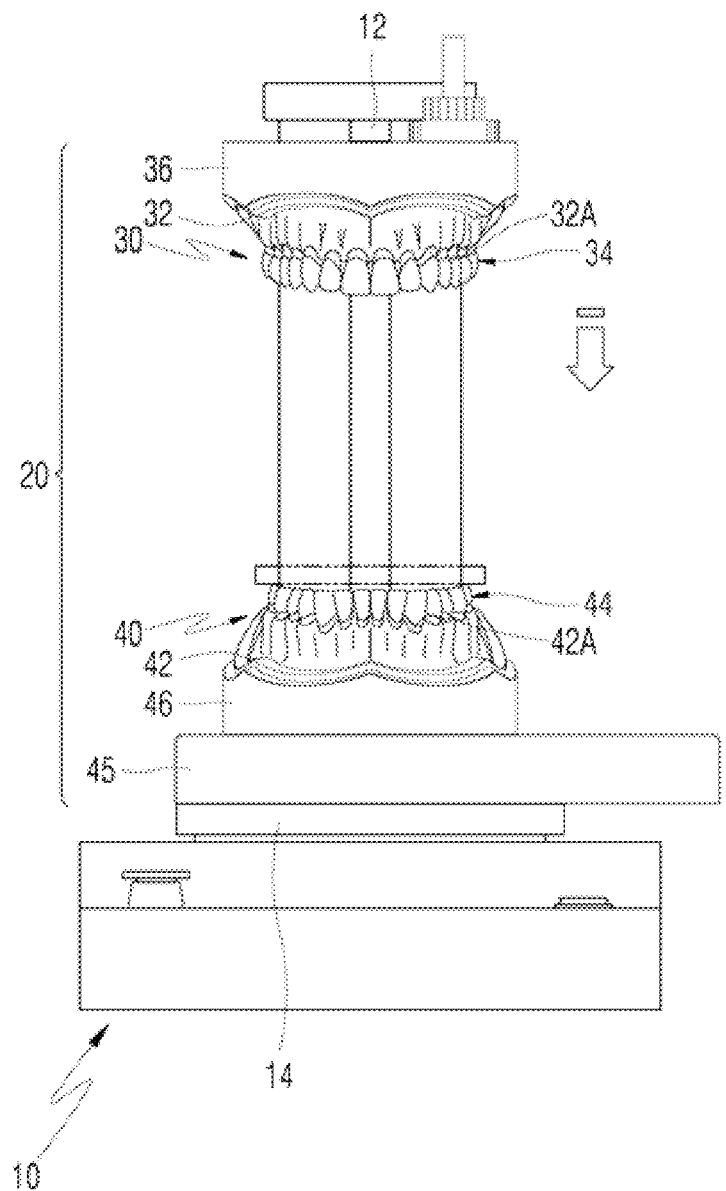
FIGS. 5 and 6 are front views illustrating a state in which the probe device for analyzing physical properties of food illustrated in FIG. 1 is installed and used in a device for analyzing physical properties of food.
Figure 6:
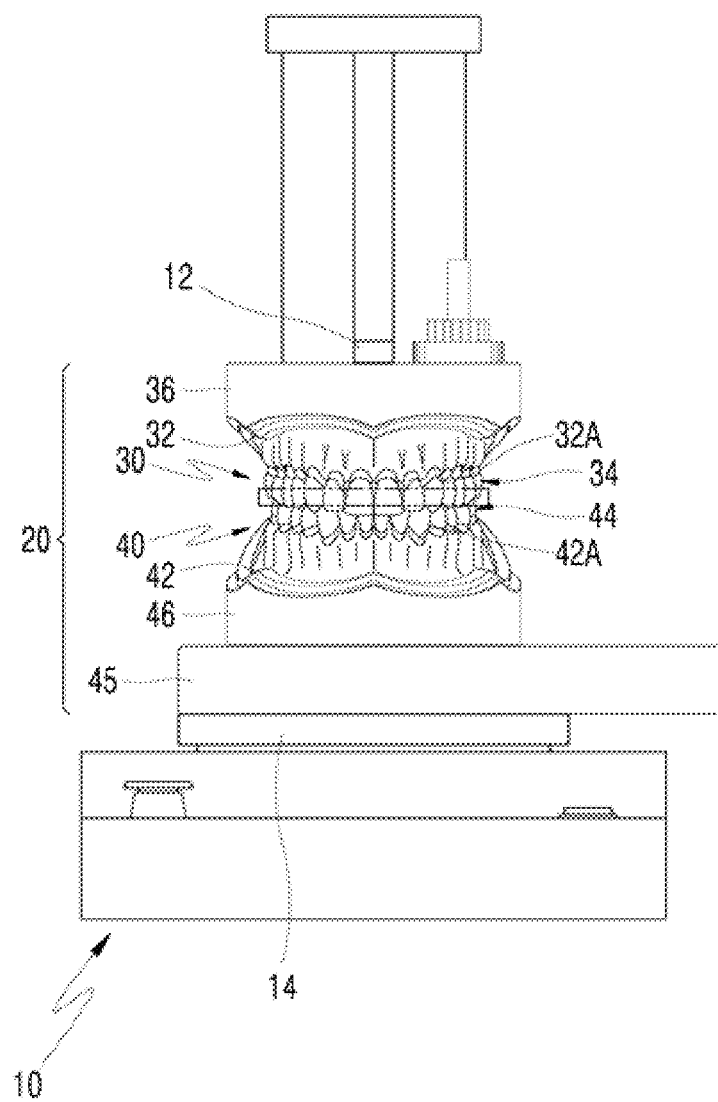

In the accompanying drawings, FIG. 1 is an exploded perspective view illustrating a probe device for analyzing physical properties of food according to a first exemplary embodiment of the present invention, FIG. 2 is a perspective view illustrating an assembled state of the probe device for analyzing physical properties of food illustrated in FIG. 1, and FIG. 3 is a front view illustrating the probe device for analyzing physical properties of food illustrated in FIG. 1. FIG. 4 is a partially enlarged cross-sectional view illustrating an upper jaw fixing unit illustrated in FIG. 1, and FIGS. 5 and 6 are front views illustrating a state in which the probe device for analyzing physical properties of food illustrated in FIG. 1 is installed and used in a device for analyzing physical properties of food.

As illustrated in FIGS. 1 to 6, a probe device 20 for analyzing physical properties of food, having a teeth form according to the present invention which is installed in a device 10 for analyzing physical properties of food to measure physical properties of food, is to more objectively and accurately measure physical properties when analyzing the physical properties of food by using probes that are formed to have the same form and the same number as those of teeth of the human body, as compared to data obtained by analysis using the general probes according to the related art.

This will be described in more detail.

The probe device 20 for analyzing physical properties of food, having a teeth form according to the present invention includes an upper jaw model part 30 formed in a shape of the upper jaw of the human body and including an upper jaw gum part 32 in which upper jaw installation holes 32A for installing respective upper jaw tooth models are each formed, and a lower jaw model part 40 formed to be occluded with the upper jaw model part 30 and including a lower jaw gum part 42 in which lower jaw installation holes 42A for installing respective lower jaw tooth models are each formed. That is, the probe device 20 having a teeth form includes the upper jaw model part 30 formed in a shape of the upper jaw of the human body and having the upper jaw installation holes 32A formed therein, and the lower jaw model part 40 formed in a shape of the lower jaw and having the lower jaw installation holes 42A formed therein.

The upper jaw gum part 32 and the lower jaw gum part 42 are formed in a shape of the upper jaw and a shape of the lower jaw of the human body, respectively, as illustrated in FIGS. 1 to 3.

Further, probes 34 having an upper jaw teeth form, of which a form and the number are the same as those of molars, canine teeth, and front teeth, are detachably coupled to the upper jaw installation holes 32A, respectively, and probes 44 having a lower jaw teeth form, of which a form and the number are the same as those of molars, canine teeth, and front teeth, are detachably coupled to the lower jaw installation holes 42A, respectively.

The upper jaw installation holes 32A have a stopper step 32B formed therein as illustrated in FIG. 4. The stopper steps 32B are a component for holding the probes 34 having an upper jaw teeth form to be seated.

The probes 34 having an upper jaw teeth form which is formed in a teeth form using a melamine synthetic resin, is configured to be similar to teeth of the human body. As illustrated in FIG. 1, the probes 34 having an upper jaw teeth form include a contact part 34A contacting the probes 44 having a lower jaw teeth form, and a coupling screw part 34B detachably coupled to the upper jaw installation hole 32A of the upper jaw gum part 32.

The probes 34 having an upper jaw teeth form are formed to have the same form, the same shape, and the same number as those of molars, canine teeth, and front teeth (adult standard).

Although not illustrated, a stopper step is formed in the lower jaw installation holes 42A, like the upper jaw installation hole 32A. The stopper step is a component for holding the probes 44 having a lower jaw teeth form to be seated.

The probes 44 having a lower jaw teeth form, which are formed in a teeth form using a melamine synthetic resin like the probes 34 having an upper jaw teeth form, is configured to be similar to teeth of the human body.

As illustrated in FIG. 1, the probes 44 having a lower jaw teeth form include a contact part 44A contacting the probes 34 having an upper jaw teeth form, and a coupling screw part 44B detachably coupled to the lower jaw installation hole 42A of the lower jaw gum part 42.

The probes 44 having a lower jaw teeth form are formed to have the same form, the same shape, and the same number as those of molars, canine teeth, and front teeth (adult standard).

Meanwhile, the upper jaw model part 30 includes an upper jaw support member 36 coupled to a lifting member 12 installed in the device 10 for analyzing physical properties of food and ascending and descending, and an upper jaw connection member 38 formed in the same shape as an upper surface area of the upper jaw gum part 32, disposed between the upper jaw support member 36 and the upper jaw gum part 32, and having a ring shape for forming an upper jaw space S1 between the upper jaw support member 36 and the upper jaw gum part 32 when the upper jaw support member 36 and the upper jaw gum part 32 are coupled to each other. That is, the upper jaw gum part 32 is coupled to a bottom surface of the upper jaw support member 36 using a bolt, or the like while interposing the upper jaw connection member 38.

The lower jaw model part 40 includes support blocks 45 installed on the table 14 of the device 10 for analyzing physical properties of food and installed to be positioned directly under the upper jaw support member 36, the lower jaw support member 46 coupled to an upper surface of the support block 45, and a lower jaw connection member 48 formed in the same shape as a bottom surface area of the lower jaw gum part 42, disposed between the lower jaw support member 46 and the lower jaw gum part 42, and having a ring shape for forming a lower jaw space S2 between the lower jaw support member 46 and the lower jaw gum part 42 when the lower jaw support member 46 and the lower jaw gum part 42 are coupled to each other. That is, the lower jaw gum part 42 is coupled to an upper surface of the lower jaw support member 46 using a bolt, or the like while interposing the lower jaw connection member 48.

Meanwhile, the upper jaw model part 30 includes an upper jaw fixing unit for fixing respective coupling screw parts 34B inserted into the upper jaw installation holes 32A. The upper jaw fixing unit includes upper jaw fixing bolts 50A including bolt holes 52A to be fastened to the coupling screw parts 34B in the upper jaw space S1 for detachably fixing the probes 34 having an upper jaw teeth form to the upper jaw gum part 32.

That is, as illustrated in FIGS. 1 and 4, the upper jaw fixing bolt 50A is inserted into the upper jaw installation hole 32A in the upper jaw space S1 and fastened to the coupling screw part 34B inserted into the upper jaw installation hole 32A to thereby fix the probes 34 having an upper jaw teeth form to the upper jaw gum part 32. In other words, in a state in which the probes 34 having an upper jaw teeth form is inserted into the upper jaw installation hole 32A and obstructed by the stopping step, the upper jaw fixing bolt 50A is inserted into the upper jaw installation hole 32A in the upper jaw space S1, and then the coupling screw part 34B is fastened to the bolt hole 52A formed in an end portion of the upper jaw fixing bolt 50A, such that the probes 34 having an upper jaw teeth form may be firmly coupled to the upper jaw gum part 32. If the upper jaw fixing bolt 50A is loosened, the probes 34 having an upper jaw teeth form may be separated from the upper jaw gum part 32.

The lower jaw model part 40 includes a lower jaw fixing unit for detachably fixing respective coupling screw parts 44B of the probes 44 having a lower jaw teeth form inserted into the lower jaw installation holes 44A. The lower jaw fixing unit includes lower jaw fixing bolts 50B including bolt holes 52B to be fastened to the coupling screw parts 44B of the probes 44 having a lower jaw teeth form in the lower jaw space S2 for fixing the probes 44 having a lower jaw teeth form to the lower jaw gum part 42. If the lower jaw fixing bolt 50B is loosened, the probe 44 having a lower jaw teeth form may be separated from the lower jaw gum part 42.

The upper jaw fixing unit and the lower jaw fixing unit having the structure as described above are to couple the probes 34 having an upper jaw teeth form and the probes 44 having a lower jaw teeth form to the upper jaw gum part 32 and the lower jaw gum part 42, respectively, and detach the probes 34 having an upper jaw teeth form and the probes 44 having a lower jaw teeth form from the upper jaw gum part 32 and the lower jaw gum part 42, respectively, as needed. That is, the upper jaw fixing unit and the lower jaw fixing unit having the structure as described above are used for selectively using only the needed probes 34 or 44 having a teeth form among the probes 34 and 44 having a teeth form including probes having a molar form, a canine form, or a front tooth form, or using all of the probes 34 and 44 having a teeth form as they are.

Meanwhile, the probe device 20 having a teeth form according to the present invention may be applied to the device for analyzing physical properties of food that has various structures. For example, as illustrated in FIG. 5, a structure in which a lifting member 12 that is vertically installed and operated to ascend and descend and the table 14 are provided may be applied, but the present invention is not limited to any one structure.

Functions of the probe device for analyzing physical properties of food, having a teeth form that is configured as described above will be described with reference to FIGS. 5 and 6.

In a state in which the upper jaw model part 30 including the probes 34 having an upper jaw teeth form is coupled to the lifting member 12 of the device 10 for analyzing physical properties of food, and the lower jaw model part 40 including the probes 44 having a lower jaw teeth form is coupled to the support block 45 installed on the table 14 of the device 10 for analyzing physical properties of food, food of which physical properties are to be measured is seated on an upper surface of the probes 44 having a lower jaw teeth form.

Then, the device 10 for analyzing physical properties of food is operated to lower the lifting member 12.

This operation allows the contact parts 34A of the probes 34 having an upper jaw teeth form to occluded with the contact parts 44A of the probes 44 having a lower jaw teeth form. In this case, the device 10 for analyzing physical properties of food measures physical properties of the food positioned between the probes 34 having an upper jaw teeth form and the probes 44 having a lower jaw teeth form through sensors embedded therein. Detailed operation and measurement operation of the device 10 for analyzing physical properties of food are known in the art, therefore, detailed description therefor will be omitted.

As such, physical properties of food may be measured by allowing occlusion between the probes 34 having an upper jaw teeth form and the probes 44 having a lower jaw teeth form in a state in which the food is positioned between the probes 34 having an upper jaw teeth form and the probes 44 having a lower jaw teeth form that are configured identical or similar to teeth of the human body, such that the physical properties of food may be more objectively and accurately measured, as compared to data measured and analyzed using the probes according to the related art such as probes having a conical form or a blade form.

Meanwhile, a user may leave only the needed probe 34 having an upper jaw teeth form and probe 44 having a lower jaw teeth form among the probes 34 having an upper jaw teeth form and the probes 44 having a lower jaw teeth form and separate the others as needed to measure physical properties of food as described above.

For example, the user may leave only the probes 34 having an upper jaw teeth form and probes 44 having a lower jaw teeth form that correspond to molars and remove the others to measure physical properties of food as described above. This is to measure and analyze the trituration effect by the chewing motion of molars, and the like.

As such, texture of food may be measured and analyzed through functions of canine teeth, front teeth, and the like as well as molars by leaving only the needed probe among the probes 34 having an upper jaw teeth form and the probes 44 having a lower jaw teeth form and removing the other probes, or by using all of the probes 34 having an upper jaw teeth form and the probes 44 having a lower jaw teeth form.

(Examplary Embodiment 2)

Figure 7:
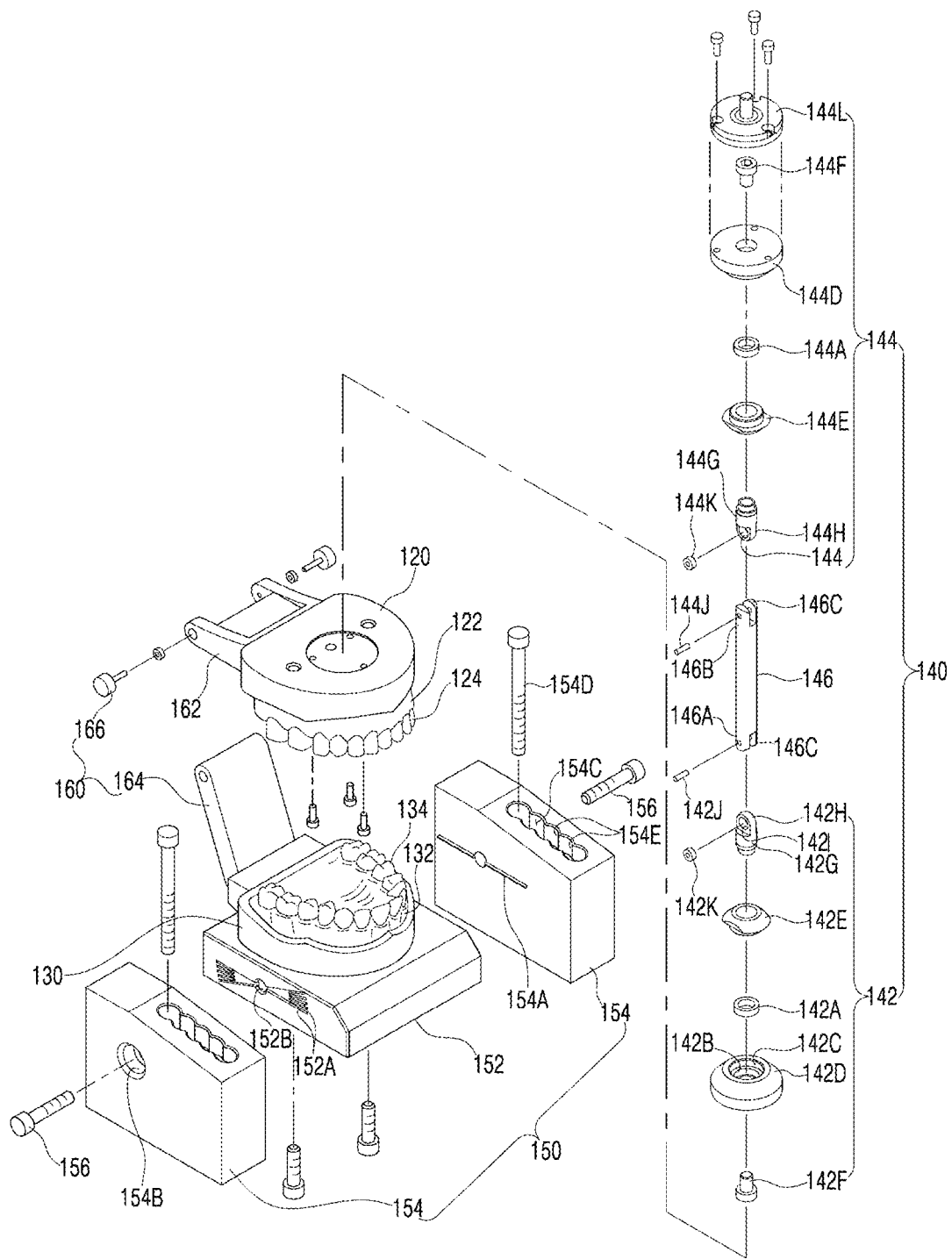
FIG. 7 is an exploded perspective view illustrating a probe device for analyzing physical properties of food, having a bearing linkage structure according to a second exemplary embodiment of the present invention.
Figure 8A:
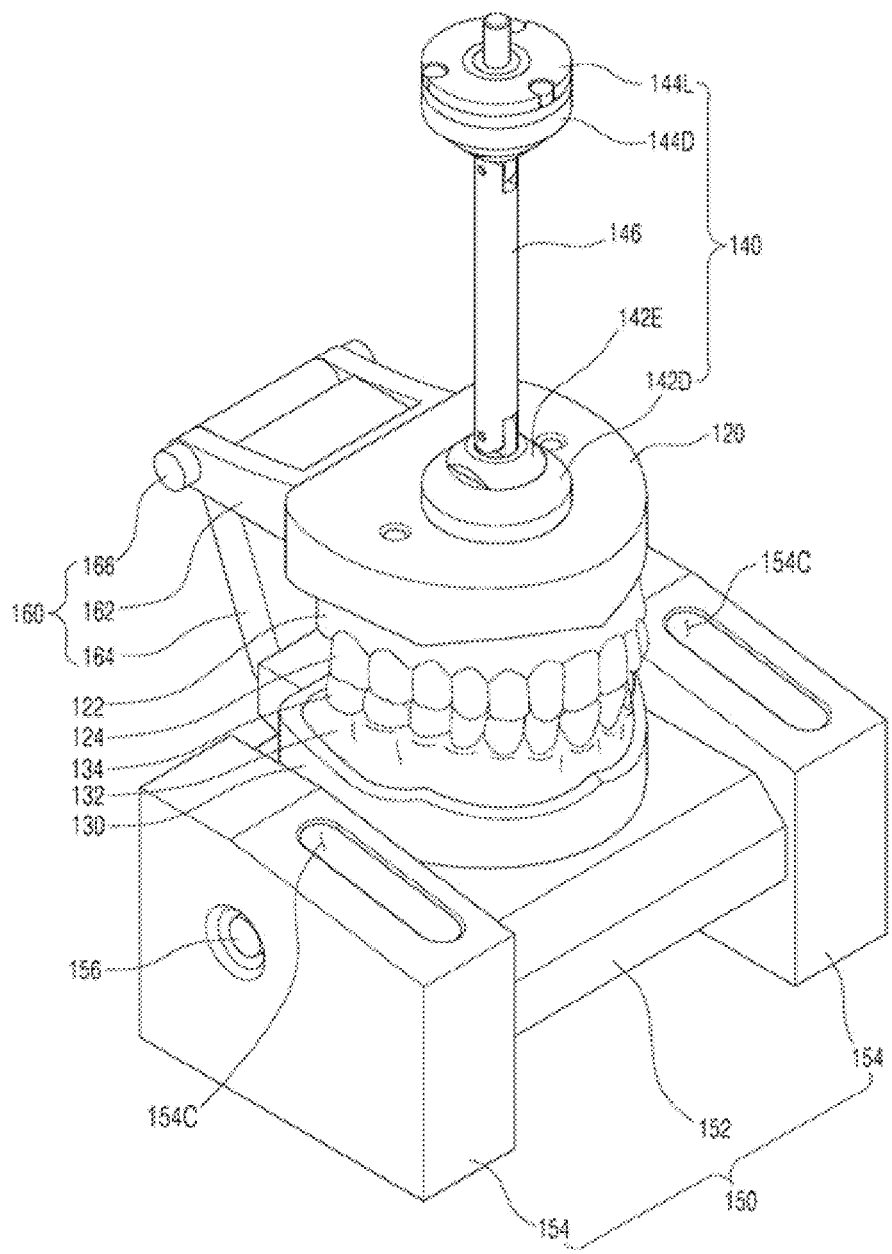
FIGS. 8A and 8B are perspective views illustrating an assembled state of the probe device for analyzing physical properties of food, having a bearing linkage structure illustrated in FIG. 7.
Figure 8B:
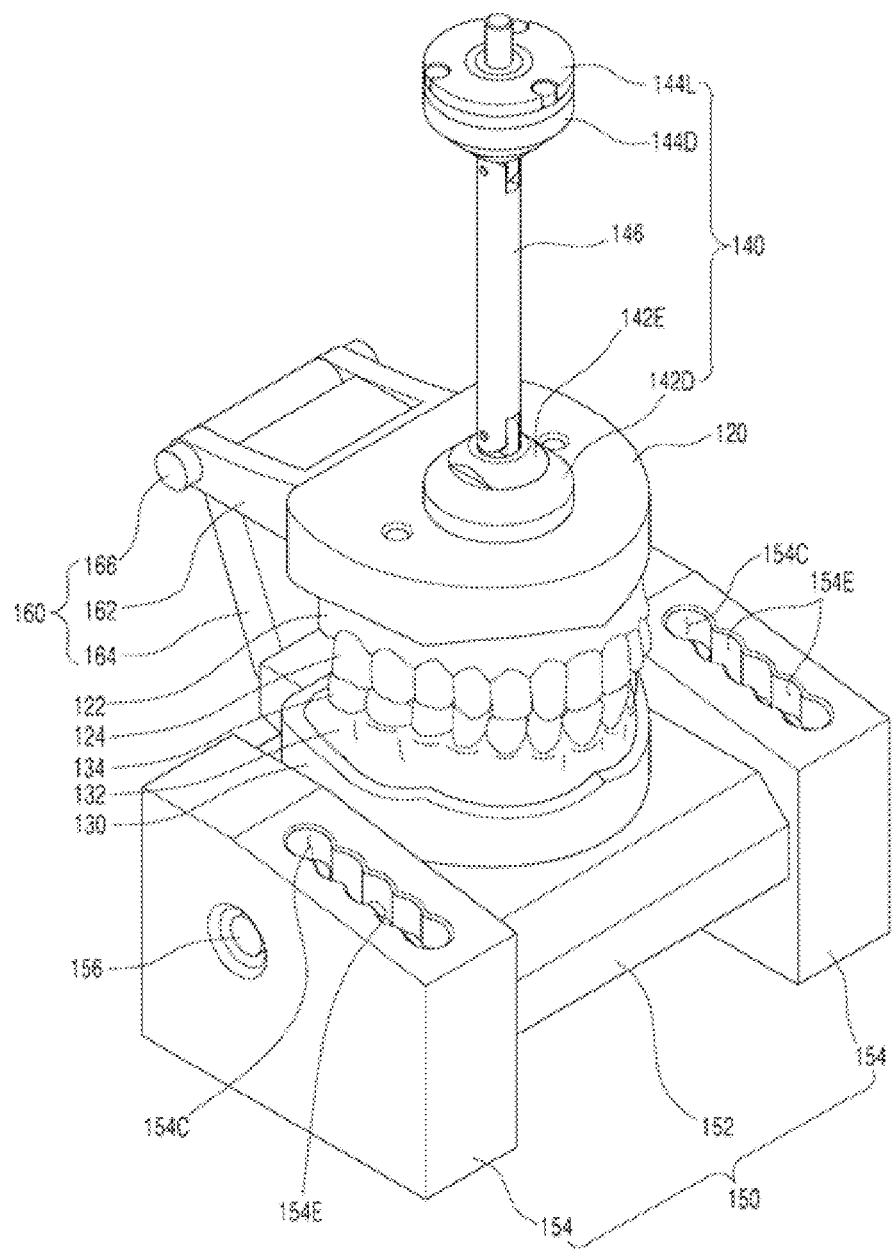
Figure 9:
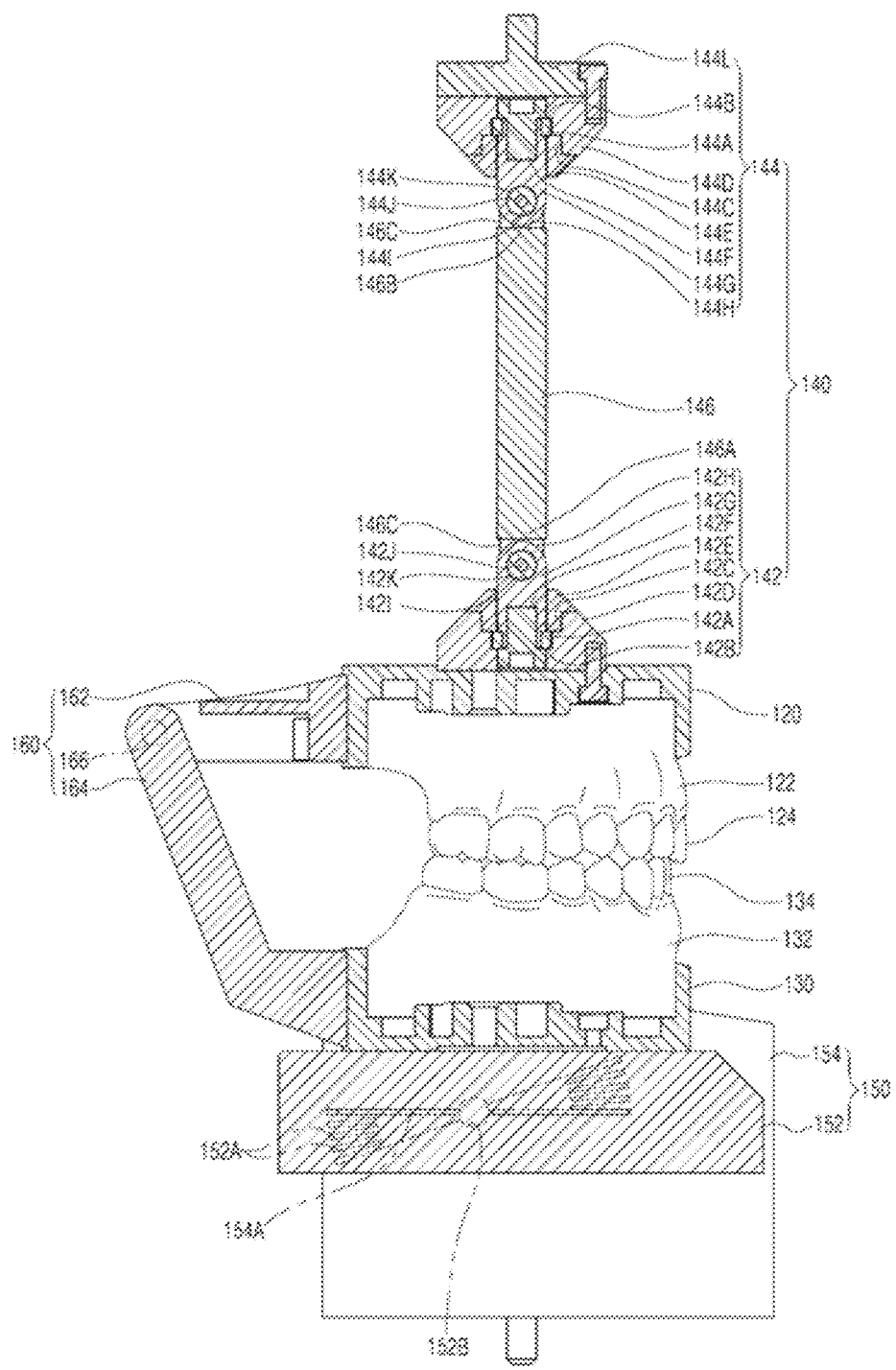
FIG. 9 is a cross-sectional view illustrating an assembled state of a connection part illustrated in FIG. 7.
Figure 10:
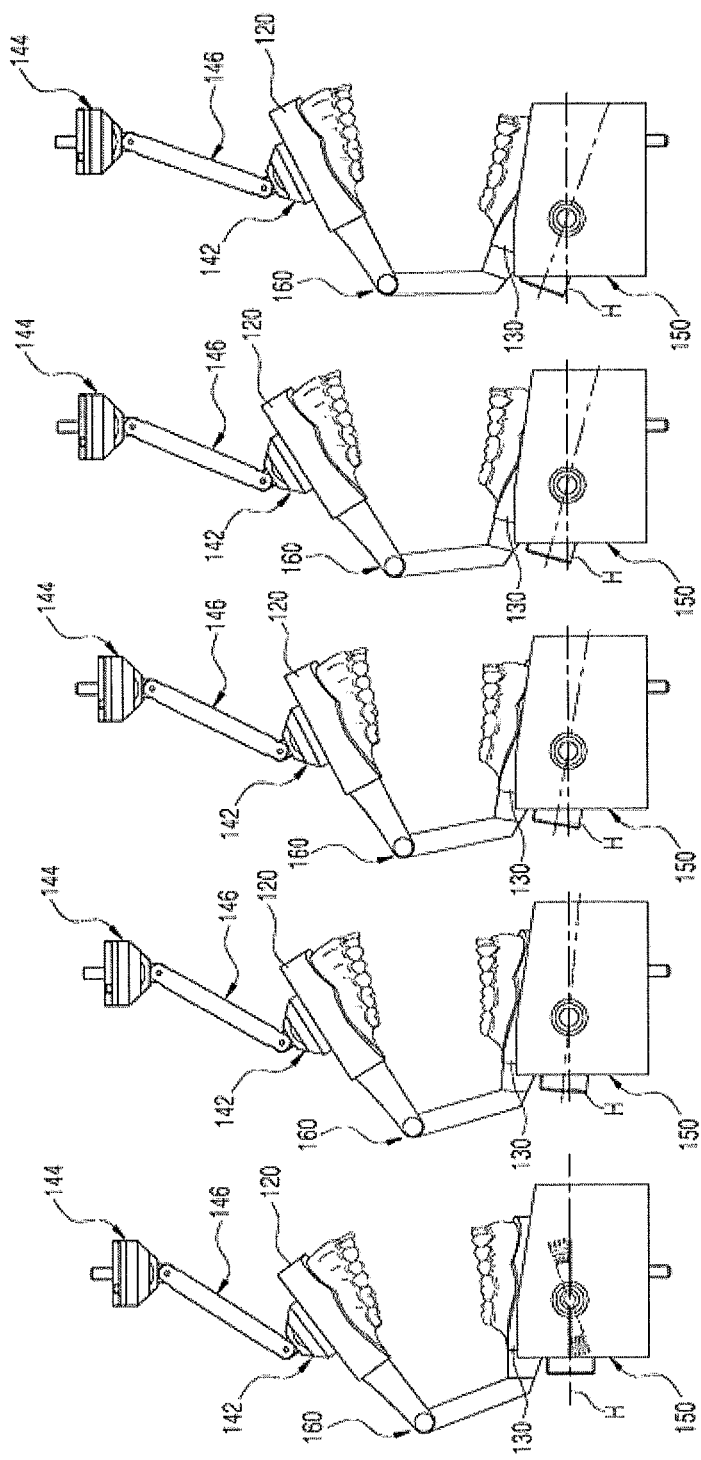
FIG. 10 shows schematic side views illustrating a state in which an angle of a central block is adjusted by an angle adjusting unit illustrated in FIG. 7.

In the accompanying drawings, FIG. 7 is an exploded perspective view illustrating a probe device for analyzing physical properties of food, having a bearing linkage structure according to a second exemplary embodiment of the present invention, FIGS. 8A and 8B are perspective views illustrating an assembled state of the probe device for analyzing physical properties of food, having a bearing linkage structure illustrated in FIG. 7, and FIG. 9 is a cross-sectional view illustrating an assembled state of a connection part illustrated in FIG. 7. Further, FIG. 10 shows schematic side views illustrating a state in which an angle of a central block is adjusted by an angle adjusting unit illustrated in FIG. 7, FIG. 11 is a side view illustrating a state before a chewing motion of the probe device for analyzing physical properties of food, having a bearing linkage structure illustrated in FIG. 7, and FIG. 12 is a side view illustrating a state after the chewing motion of the probe device for analyzing physical properties of food, having a bearing linkage structure illustrated in FIG. 7.

As illustrated in FIGS. 7 to 9, a probe device for analyzing physical properties of food, having a bearing linkage structure according to the present invention is to analyze physical properties of food through a chewing motion similar to a chewing motion of the human body and includes an upper jaw installation part 120 including an upper jaw model 122 in which respective upper jaw tooth models 124 are installed, and coupled to a pressurizing member 114 of a press device 112 that vertically reciprocates, a lower jaw installation part 130 including a lower jaw model 132 in which lower jaw tooth models 134 are installed, and coupled to the upper jaw installation part 120 by a shaft coupling part 160 so that the lower jaw model 132 is occluded with the upper jaw model 122, and a base 150 on which the lower jaw installation part 130 is installed and supported.

Hereinafter, each component will be described in more detail.

Figure 11:
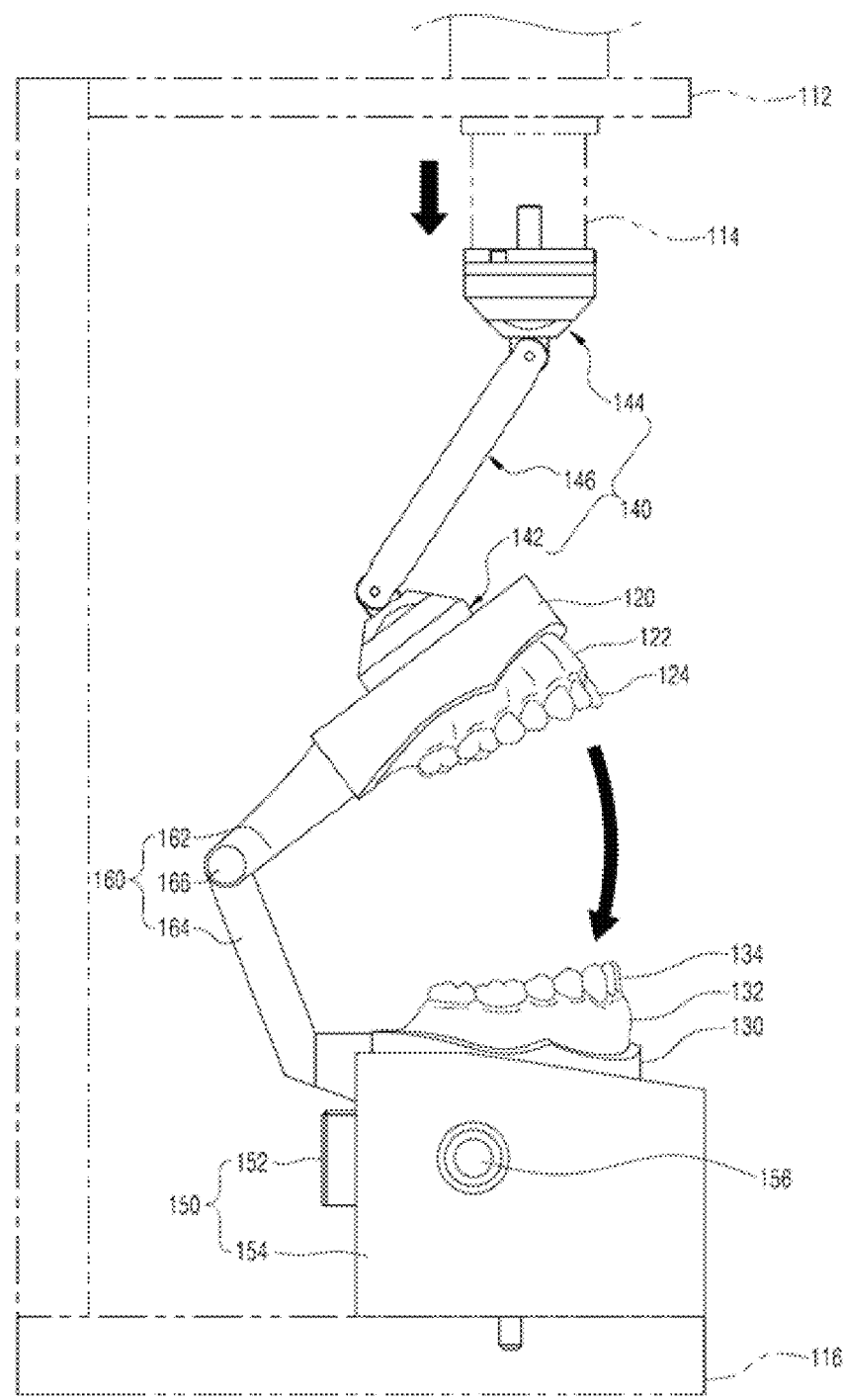
FIG. 11 is a side view illustrating a state before a chewing motion of the probe device for analyzing physical properties of food, having a bearing linkage structure illustrated in FIG. 7.
Figure 12:
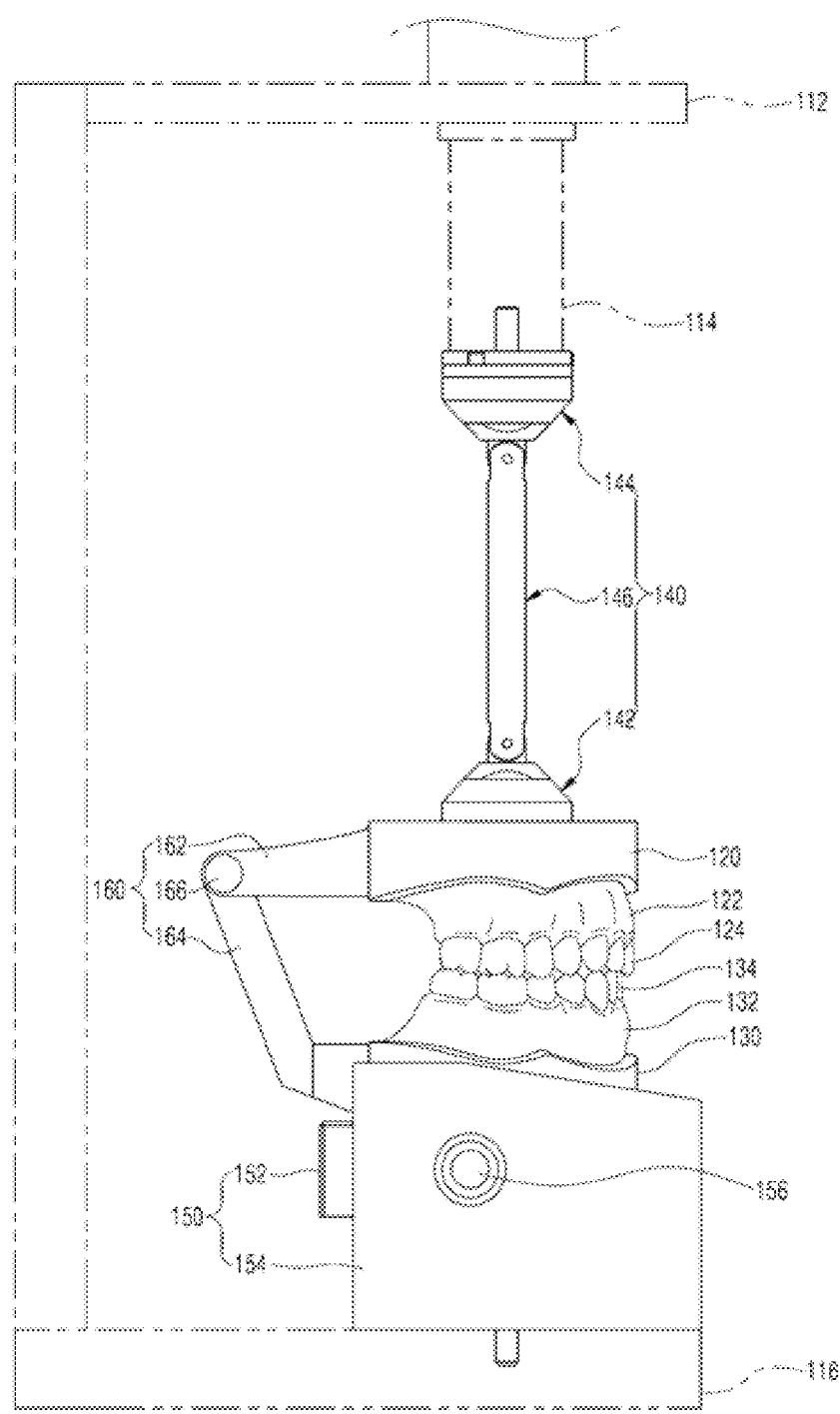
FIG. 12 is a side view illustrating a state after the chewing motion of the probe device for analyzing physical properties of food, having a bearing linkage structure illustrated in FIG. 7.

As illustrated in FIGS. 11 and 12, the press device 112 is configured to lift and lower the pressurizing member 114 provided at an upper area thereof, and is provided with a bottom plate 116 on which the base 150 is seated at a lower area thereof. Although not illustrated, a sensor for sensing a degree of pressurization of the pressurizing member 114, a control part, and the like are installed in the press device 112.

The upper jaw installation part 120 has a structure in which the upper jaw model 122 is coupled to a bottom surface the upper jaw installation part 120, and one end of an upper connection member 162 constituting a shaft coupling part 160 is coupled to a rear surface of the upper jaw installation part 120 using a bolt. A plurality of coupling holes for coupling the upper jaw model 122 so that a position of the upper jaw model 122 may be varied are formed in the bottom surface of the upper jaw installation part 120. The position of the upper jaw model 122 may be adjusted and fixed by the plurality of coupling holes.

The lower jaw installation part 130 has a structure in which the lower jaw model 132 is coupled to an upper surface the lower jaw installation part 120, and one end of a lower connection member 164 constituting the shaft coupling part 160 is coupled to a rear surface of the lower jaw installation part 130 using a bolt. A plurality of coupling holes for coupling the lower jaw model 132 so that a position of the lower jaw model 132 may be varied are formed in the lower surface of the lower jaw installation part 130. The position of the lower jaw model 132 may be adjusted and fixed by the plurality of coupling holes.

The upper jaw installation part 120 and the lower jaw installation part 130 are shaft-coupled by the shaft coupling part 60. The shaft coupling part 160 includes the upper connection member 162 coupled to the rear surface of the upper jaw installation part 120 and the lower connection member 164 coupled to the rear surface of the lower jaw installation part 130 described above, and a connection shaft 166 shaft-coupling the upper connection member 162 and the lower connection member 164 by penetrating through each of the other ends of the upper connection member 162 and the lower connection member 164. In this case, the upper connection member 162 and the lower connection member 164 have a structure extending toward a rear side (where the tooth models are not installed) at a predetermined length, specifically, as illustrated in FIGS. 7 to 8B, the lower connection member 164 has a structure in which a horizontal part is formed at an area adjacent to the lower jaw installation part 130, and an inclined part that is inclined toward the upper connection member 162 is formed at an end portion of the horizontal part. This is to form a predetermined interval such that the upper jaw installation part 120 and the lower jaw installation part 130 are parallel to each other during the chewing motion.

The connection part 140 connects the upper jaw installation part 120 and the pressurizing member 114 to each other to transfer pressurizing force of the pressurizing member 114 to the upper jaw installation part 120. The connection part 140 includes a lower bearing part 142 coupled to an upper surface of the upper jaw installation part 120, an upper bearing part 144 coupled to the pressurizing member 114, and a connection rod 146 having both ends each coupled to the upper bearing part 144 and the lower bearing part 142 so as to be freely bent. That is, the connection part 140 is configured to allow upper and lower connection regions of the connection rod 146 to be multiply bent by the pressurizing force of the pressurizing member 114 when the pressurizing member 114 ascends and descends, thereby making the chewing motion of the upper jaw installation part 120 and the lower jaw installation part 130 more natural.

The connection part 140 will be described in more detail.

The lower bearing part 142 includes a first bearing housing 142D and a first shaft joint 142G, the first bearing housing 142D having a first bearing seating step 142B on which a first bearing 142A is seated and a first cover seating step 142C on which a hollowed first bearing cover 142E is seated that are formed therein, and being coupled to the upper surface of the upper jaw installation part 120, and the first shaft joint 142G being coupled with a first coupling bolt 142F that is inserted from a bottom surface of the first bearing housing 142D in a state in which one end of the first shaft joint 142G is inserted into the first bearing cover 142E to be integrated with the first bearing housing 142D while rotation of the first shaft joint 142G itself is supported by the first bearing 142A, and having a first joint 142H formed at the other end of the first shaft joint 142G and including a shaft hole 142I for coupling the first joint 142H to a lower end portion 146A of the connection rod 146 using a shaft 142J.

In this case, a yoke part 146C to which the first joint 142H is inserted and rotatably coupled using the shaft 142J is formed at the lower end portion 146A of the connection rod 146.

Further, a joint bearing 142K having a bushing form is installed between the above described shaft 142J and shaft hole 142I.

In the lower bearing part 142 having the above described structure, the lower end portion 146A of the connection rod 146 may rotate by the first bearing 142A and be bent at a predetermined angle based on the shaft 142J by the joint bearing 142K. That is, the first bearing 142A supports the rotation of the first shaft joint 142G itself, and the joint bearing 142K supports the bending rotation of the first shaft joint 142G.

The upper bearing part 144 has a form and a structure that are symmetrical to the lower bearing part 142 and includes a second bearing housing 144D and a second shaft joint 144G, the second bearing housing 142D having a second bearing seating step 144B on which a second bearing 144A is seated and a second cover seating step 144C on which a hollowed second bearing cover 144E is seated that are formed therein, and being coupled to a bottom surface of the pressurizing member 114, and the second shaft joint 144G being coupled with a second coupling bolt 144F that is inserted from an upper surface of the second bearing housing 144D in a state in which one end of the second shaft joint 144G is inserted into the second bearing cover 144E to be integrated with the second bearing housing 142D while rotation of the second shaft joint 142G itself is supported by the second bearing 144A, and having a second joint 144H formed at the other end of the second shaft joint 144G and including a shaft hole 144I for coupling the second joint 142H to an upper end portion 146B of the connection rod 146 using a shaft 144J. The upper surface of the second bearing housing 144D is coupled to the bottom surface of the pressurizing member 114 by a coupling bracket 144L.

In this case, a yoke part 146C to which the second joint 144H is inserted and rotatably coupled using the shaft 144J is formed at the upper end portion 146B of the connection rod 146. Further, a joint bearing 144K having a bushing form is installed between the above described shaft 144J and shaft hole 144I. In the upper bearing part 144 having the above described structure, the upper end portion 146B of the connection rod 146 may rotate by the second bearing 144A and be bent at a predetermined angle based on the shaft 144J by the joint bearing 144K. That is, the second bearing 144A supports the rotation of the second shaft joint 144G itself, and the joint bearing 144K supports the bending rotation of the second shaft joint 144G.

In the connection part 140, the lower end portion 146A of the connection rod 146 is bendably and rotatably supported by the lower bearing part 142 and the upper end portion 146B of the connection rod 146 is bendably and rotatably supported by the upper bearing part 144, such that an ascending and descending operation of the pressurizing member 114 may be interlocked with the chewing motion of the upper jaw installation part 120 and the lower jaw installation part 130. That is, the upper jaw installation part 120 and the lower jaw installation part 130 are not vertically occluded, but flexibility may be given so that the chewing motion of the upper jaw installation part 120 and the lower jaw installation part 130 that is similar to that of the jaw joint of the human body may be made.

On the base 150, the lower jaw installation part 130 installed and supported. The base 150 includes a central block 152 on which the lower jaw installation part 130 is seated and coupled, and side blocks 154 each coupled to both sides of the central block 152 to support the central block 152.

The base 150 is provided with an angle adjusting unit for adjusting the central block 152 to which the lower jaw installation part 130 is coupled within a predetermined angle based on a horizontal line. That is, an angle at which the central block 152 is inclined toward the front based on the horizontal line may be adjusted within a predetermined range.

The angle adjusting unit will be described in detail.

Then angle adjusting unit includes a plurality of angle adjusting grooves 152A formed at one side surface or both side surfaces of the central block 152 to which the side blocks 154 are coupled, and angle adjusting protrusions 154A selectively inserted into the angle adjusting grooves 152A and formed at the side block 154 in a position corresponding to the angle adjusting groove 152A to fix the angle of the central block 152. That is, as illustrated in FIG. 7, the angle adjusting grooves 152A are formed at one side surface or both side surfaces of the central block 152, and the angle adjusting protrusions 154A selectively inserted into each of the angle adjusting grooves 152A are formed at a surface of the side block 154 contacting a surface at which the angle adjusting grooves 152A are formed.

In this case, adjusting the angle of the central block 152 is enabled by fastening a coupling bolt 156 for coupling the side block 154 to the central block 152 to a fastening hole 152B formed at the central block 152 in a state in which the angle adjusting protrusions 154A are inserted into the angle adjusting grooves 152A. That is, both side blocks 154 may be coupled to the central block 152 and the angle of the central block 152 may be fixed to an adjusted angle by fastening and tightening the coupling bolt 156 in a state in which the angle of the central block 152 is adjusted.

Meanwhile, the angle adjusting grooves 152A are radially disposed based on the fastening hole 152B, and disposed at both sides of the fastening hole 152B. Further, the angle adjusting grooves 152A are formed in a fan shape as illustrated in FIGS. 7 and 10.

The angle adjusting protrusions 154A are disposed at both sides of a bolt through hole 154B formed at the side block 154 so that the coupling bolt 156 penetrates therethrough.

As such, since the angle adjusting grooves 152A or the angle adjusting protrusions 154A are provided at both sides of the fastening hole 152B and the bolt through hole 154B, the angle of the central block 152 may be stably fixed.

Meanwhile, in the side blocks 154, as illustrated in FIG. 8A, long holes 154C for sliding the central block 152 forward or backward when the pressurizing member 114 is operated to make the connection part 140 operate the upper jaw installation part 120 so that the chewing motion of the upper jaw model 122 and the lower jaw model 132 is performed are each formed in a vertical direction, and long bolts 154D for coupling the side blocks to the bottom plate 116 of the probe device penetrate through the long holes 154C to be installed. Here, the long bolt 154D may be installed so that a head portion thereof is exposed to an upper surface of the side block 154.

A function of the above described probe device for analyzing physical properties of food, having a bearing linkage structure according to the present invention will be described.

In a state in which both side blocks 154 of the base 150 are fastened and fixed to the bottom plate 116 by the long bolt 154D penetrating through the long hole 154C, and the pressurizing member 114 and the upper jaw installation part 120 are connected to each other by the connection part 140, the upper jaw model 122 is installed under the upper jaw installation part 120 and the lower jaw model 132 is installed on the lower jaw installation part 130.

Here, the upper jaw tooth models 124 are provided in the upper jaw model 122 and the lower jaw tooth models 134 are installed in the lower jaw model 132. These tooth models 124 and 134 are replaceably installed in the upper jaw model 122 and the lower jaw model 132.

Further, as illustrated in FIG. 10, the angle adjusting protrusions 154 are inserted into the angle adjusting grooves 152A at a predetermined angle by loosening the coupling bolt 156 to loose both side blocks 154 and the central block 152 and adjusting the angle of the central block 152. Then, the adjusted angle of the central block 152 is fixed by tightening the coupling bolt 156. By such angle adjustment, the angle of the central block 152 may be adjusted to various angles as illustrated in the views of FIG. 10. That is, the angle of the central block 152 may be adjusted from 0° to 25° based on the horizontal line H.

As such, adjusting the central block 152 to be inclined forward at a predetermined angle is to make the chewing motion of the upper jaw installation part 120 and the lower jaw installation part 130 similar to the chewing motion of the jaw joint of the human body. That is, this is to compensate a problem of the probe device according to the related art that the chewing motion is performed in a manner that an upper jaw model vertically descends in a state in which a lower jaw model is horizontally fixed, which is far from the real chewing motion of the human body.

Meanwhile, the long bolts 154D are fastened to the bottom plate 116 through the long holes 154C of respective side blocks 154. Here, the side blocks 154 may be slid within the range of the long holes 154C so that the pressurizing force of the connection part 140 may be perfectly vertically transferred to the upper jaw installation part 120 at the time of the chewing motion of the upper jaw installation part 120 and the lower jaw installation part 130. That is, when the upper jaw installation part 120 descends and pressurizes the lower jaw installation part 130 to perform the chewing motion, the side blocks 154 constituting the base 150 are slid within the range of the long holes 154C to move forward or backward, thereby allowing the smooth chewing motion of the upper jaw model 122 and the lower jaw model 132.

To this end, it is preferable that the long holes 154C are formed in a shape in which position determining grooves 154E are removed as illustrated in FIG. 8A.

Further, in order to adjust and fix the position of the side blocks 154 so that the side blocks 154 are not slid, a plurality of position determining grooves 154E may be formed in the long holes 154C as illustrated in FIG. 7 or 8A to fasten the long bolt 154D to the bottom plate 116 through a desired position determining groove 154E.

When the angle and the position of the base 150 are fixed as described above, food to be measured and analyzed is disposed between the upper jaw model 122 and the lower jaw model 132, and the press device 122 is operated.

When the press device 122 is operated, the pressurizing member 114 descends to pressurize the connection part 140.

That is, as illustrated in FIG. 11, in a state before the pressurizing member 114 is operated, when the pressurizing member 114 descends and pressurizes the connection member 140, the pressurizing force of the pressurizing member 114 is transferred to the upper jaw installation part 120 through the connection rod 146 of the connection part 140, thus the upper jaw installation part 120 rotates toward the lower jaw installation part 130 based on the connection shaft 166. In this case, when the pressurizing member 114 descends, the upper bearing part 144 and the upper end portion 146B of the connection rod 146, and the lower bearing part 142 and the lower end portion 146A of the connection rod 146 are freely bent within a predetermined range.

Because of such structure, connection between the pressurizing member 114 and the upper jaw installation part 120 is maintained even in a state in which a central axial line of the pressurizing member 114 and a central vertical line of the upper jaw installation part 120 are not matched with each other since the upper jaw installation part 120 is lifted upwardly based on the connection shaft 166 of the shaft coupling part 160, and when the pressurizing member 114 descends, as illustrated in FIG. 12, the pressurizing force of the pressurizing member 114 is transferred to the upper jaw installation part 120 so that the upper jaw model 122 and the lower jaw model 132 are occluded with each other by a predetermined pressure thereby allowing the chewing motion to be performed.

Further, even when the pressurizing member 114 descends in a state in which the angle of the central block 152 of the base 150 is adjusted to incline the central block 152 forward so that the lower jaw model 132 is inclined forward, and the upper jaw installation part 120 is lifted upwardly in an inclined manner by the shaft coupling part 160 as illustrated in FIG. 10, the respective tooth models 124 and 134 of the upper jaw model 122 and the lower jaw model 132 horizontally contact and are occluded with each other by the connection part 140 that may be multiply bent. That is, interlocking of the connection part 140 and the shaft coupling part 160 makes the chewing motion of the upper jaw installation part 120 and the lower jaw installation part 130 similar to the chewing motion of the jaw joint of the human body, such that physical properties of food disposed between the respective tooth models 124 and 134 may be measured under a condition similar to that of the chewing motion of the human body.

Further, the first bearing 142A and the second bearing 144A of the connection part 140 support the rotation of the first shaft joint 142G and the second shaft joint 144G themselves, and the joint bearings 142K and 144K each support the bending rotation of the connection rod 146, thereby making the chewing motion of the upper jaw installation part 120 and the lower jaw installation part 130 by the ascending and descending operation of the pressurizing member 114 natural.

(Examplary Embodiment 3)

Figure 13:
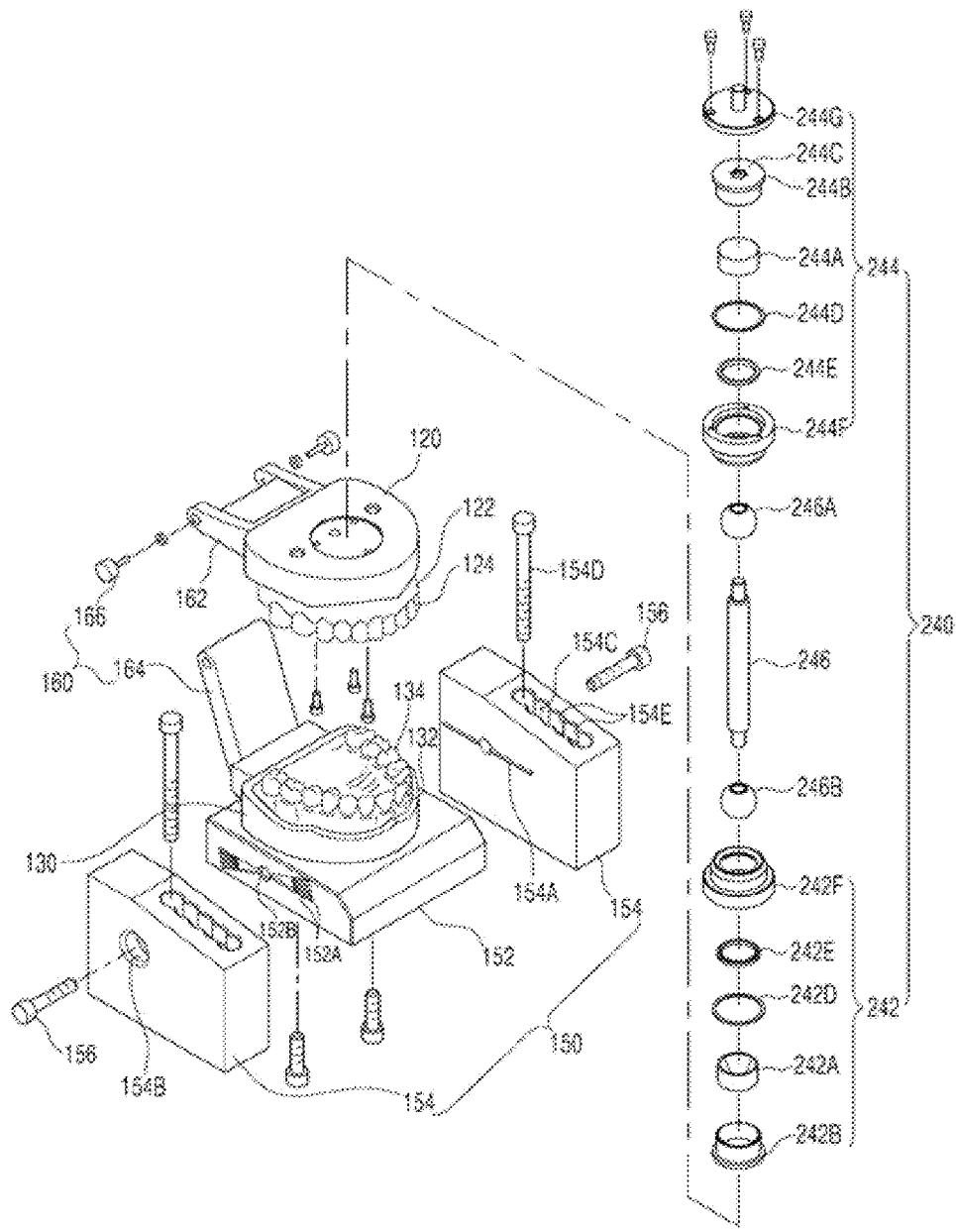
FIG. 13 is an exploded perspective view illustrating a probe device for analyzing physical properties of food, having a ball head linkage structure according to a third exemplary embodiment of the present invention.
Figure 14A:
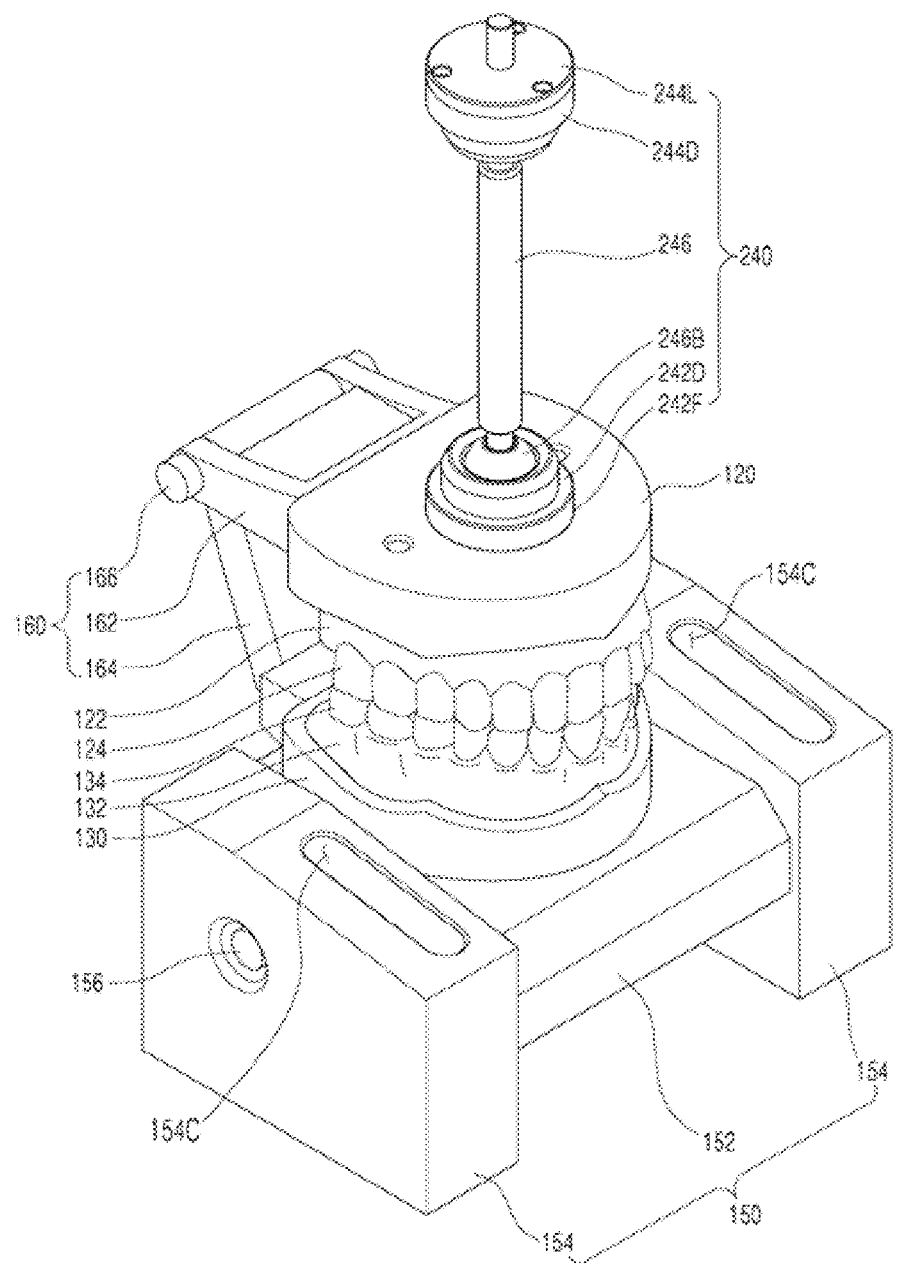
FIGS. 14A and 14B are perspective views illustrating an assembled state of the probe device for analyzing physical properties of food, having a ball head linkage structure illustrated in FIG. 13.
Figure 14B:
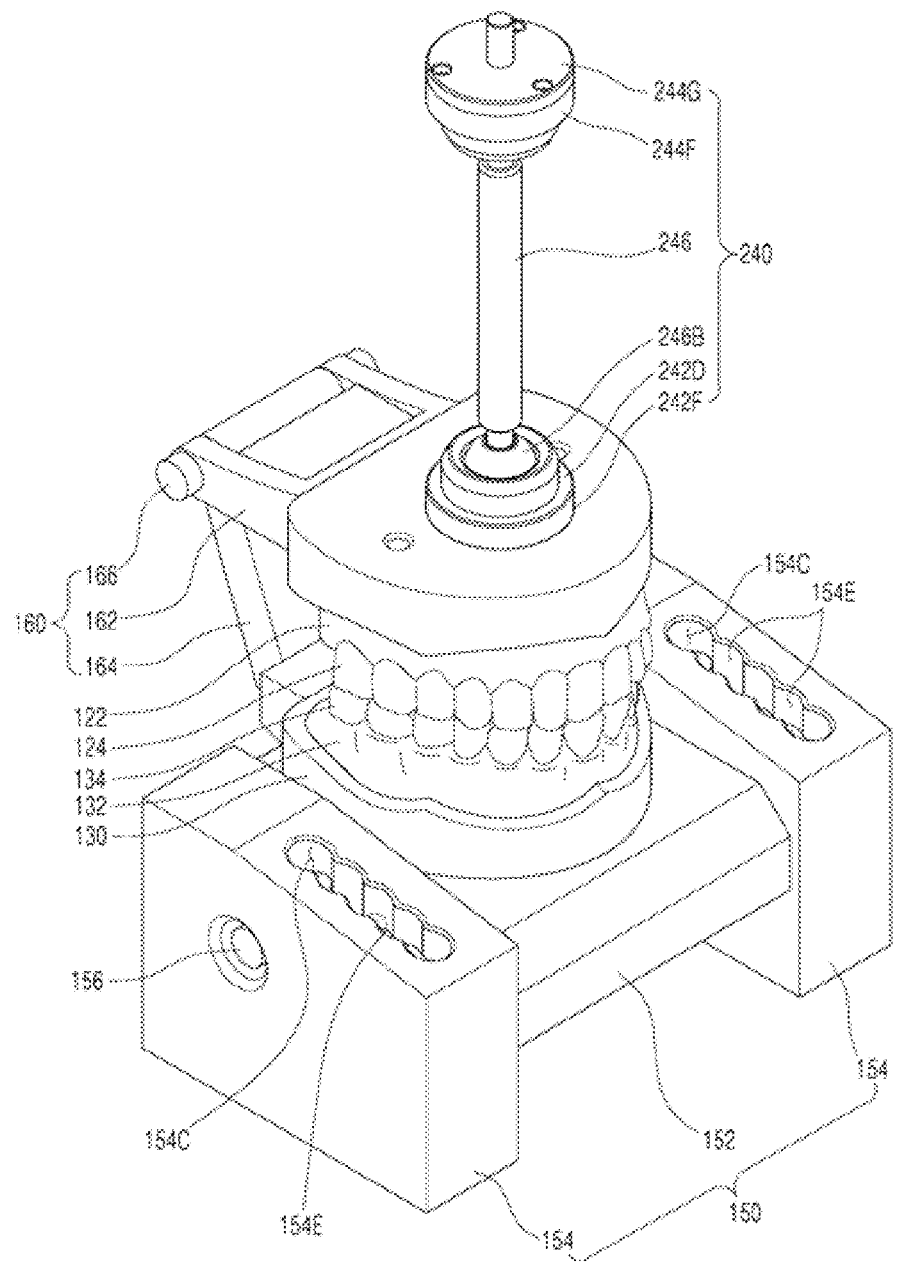
Figure 15:
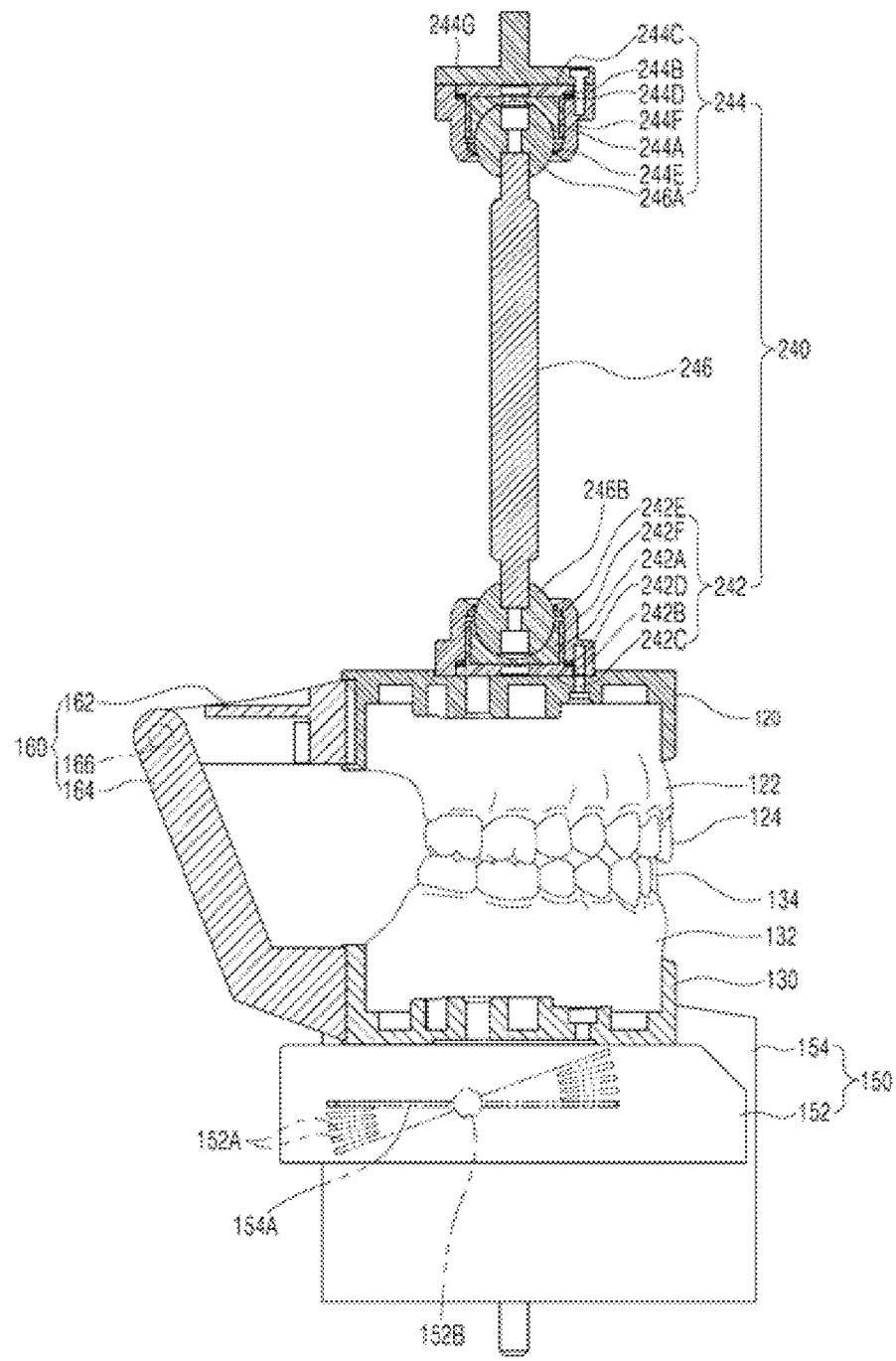
FIG. 15 is a cross-sectional view illustrating an assembled state of a connection part illustrated in FIG. 13.
Figure 16:
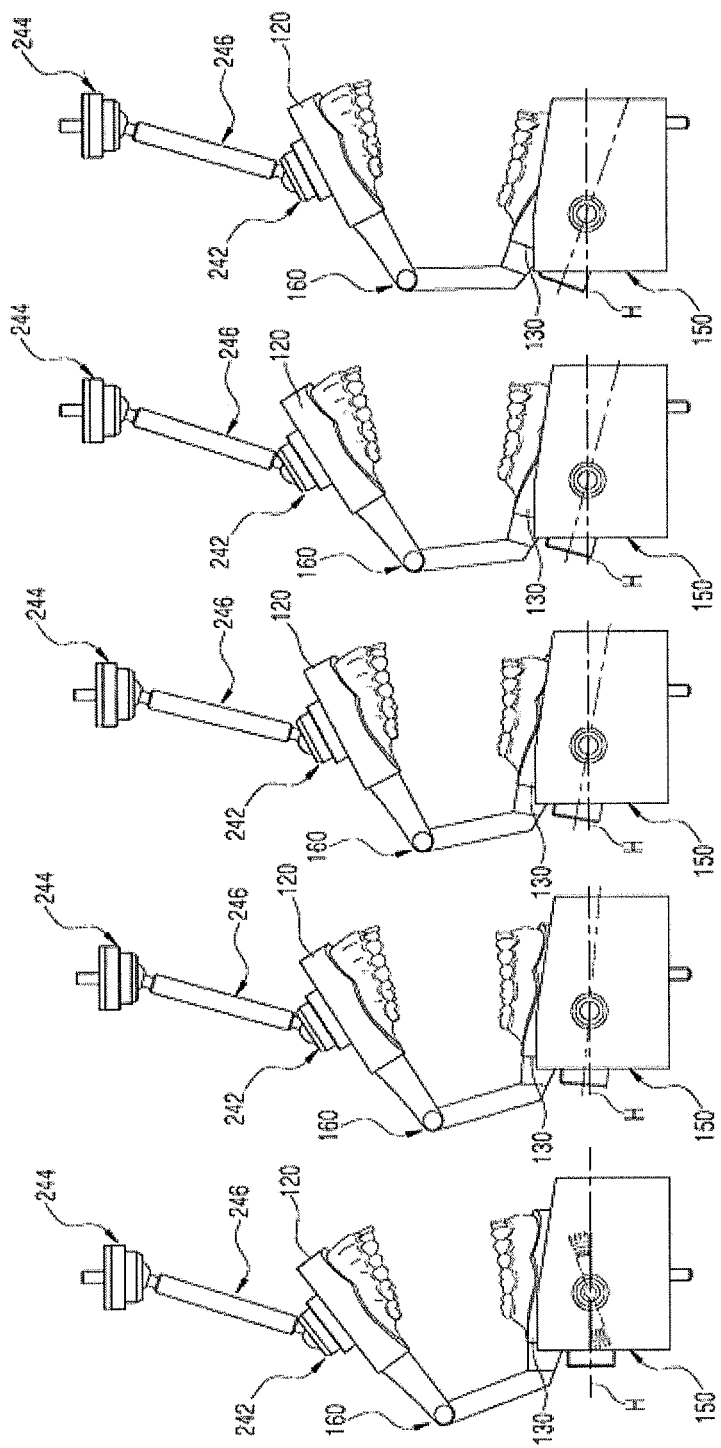
FIG. 16 shows schematic side views illustrating a state in which an angle of a central block is adjusted by an angle adjusting unit illustrated in FIG. 13.
Figure 17:
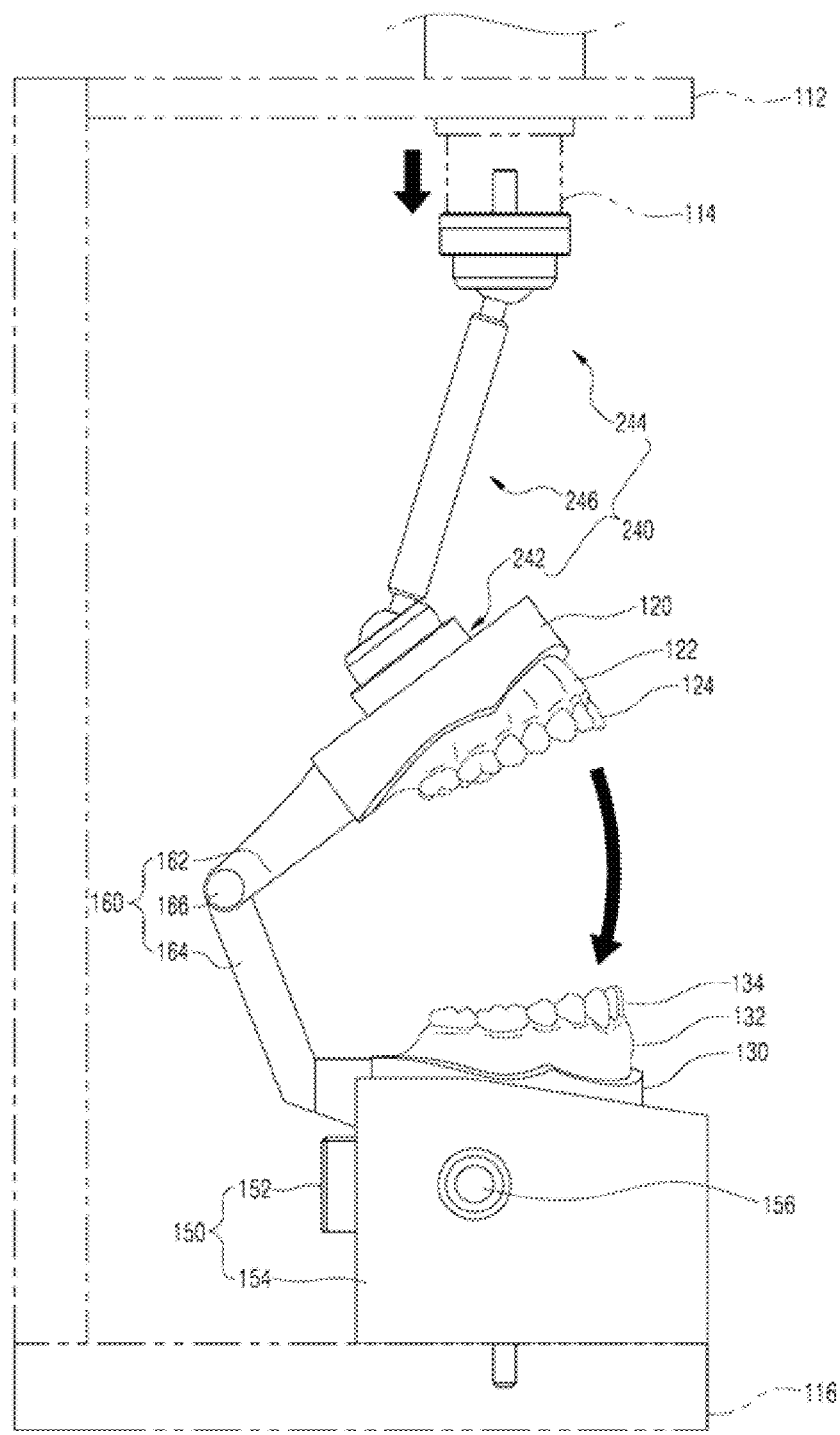
FIG. 17 is a side view illustrating a state before a chewing motion of the probe device for analyzing physical properties of food, having a ball head linkage structure illustrated in FIG. 13.
Figure 18:
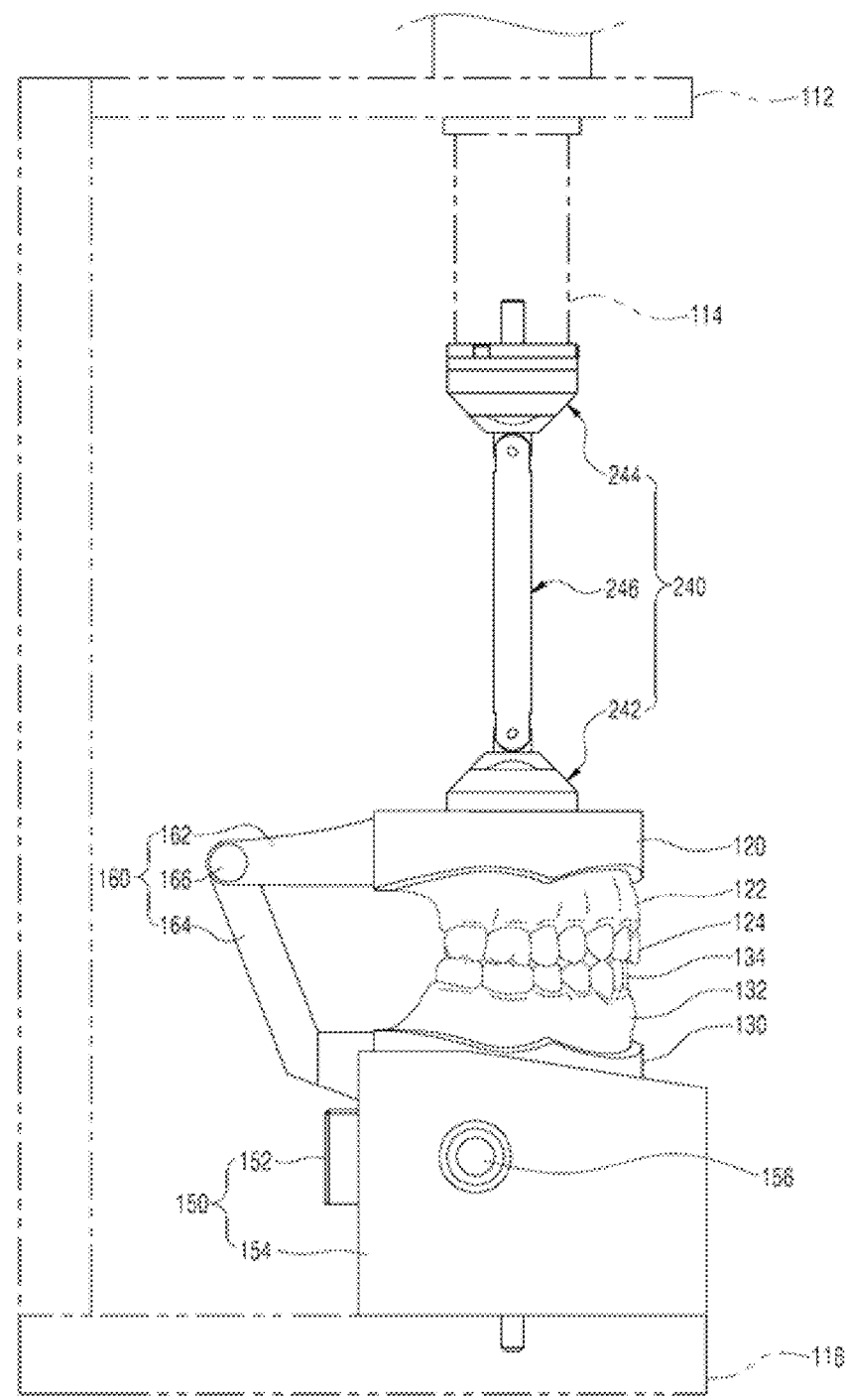
FIG. 18 is a side view illustrating a state after the chewing motion of the probe device for analyzing physical properties of food, having a ball head linkage structure illustrated in FIG. 13.

In the accompanying drawings, FIG. 13 is an exploded perspective view illustrating a probe device for analyzing physical properties of food, having a ball head linkage structure according to a third exemplary embodiment of the present invention, FIGS. 14A and 14B are perspective views illustrating an assembled state of the probe device for analyzing physical properties of food, having a ball head linkage structure illustrated in FIG. 13, and FIG. 15 is a cross-sectional view illustrating an assembled state of a connection part illustrated in FIG. 13. Further, FIG. 16 shows schematic side views illustrating a state in which an angle of a central block is adjusted by an angle adjusting unit illustrated in FIG. 13, FIG. 17 is a side view illustrating a state before a chewing motion of the probe device for analyzing physical properties of food, having a ball head linkage structure illustrated in FIG. 13, and FIG. 18 is a side view illustrating a state after the chewing motion of the probe device for analyzing physical properties of food, having a ball head linkage structure illustrated in FIG. 13.

As illustrated in FIGS. 13 to 18, a probe device for analyzing physical properties of food, having a ball head linkage structure according to a third exemplary embodiment of the present invention includes an upper jaw installation part 120, a lower jaw installation part 130, a connection part 240, a base 150, and a shaft coupling part 160. The components except for the connection part 240 are the same as the components in the second exemplary embodiment, thus description therefor will be omitted, and only configuration of the connection part 240 of which a reference numeral is changed will be described.

The connection part 240 connects the upper jaw installation part 120 and the pressurizing member 114 to each other to transfer the pressurizing force of the pressurizing member 114 to the upper jaw installation part 120. The connection part 140 includes a lower ball head part 242 coupled to the upper surface of the upper jaw installation part 120, an upper ball head part 244 coupled to the pressurizing member 114, and a connection rod 246 having both ends each coupled to the upper ball head part 244 and the lower ball head part 242 so as to be freely bent. That is, the connection part 240 is configured to allow upper and lower connection regions of the connection rod 246 to be inclined at an angle of about 0 to 80° by the pressurizing force of the pressurizing member 114 when the pressurizing member 114 ascends and descends, thereby making the chewing motion of the upper jaw installation part 120 and the lower jaw installation part 130 more natural.

The connection part 240 will be described in more detail.

The connection rod 246 has an upper end portion and a lower end portion to which a first joint ball 246A and a second joint ball 246B are each coupled, has a function of connecting the pressurizing member 114 and the upper jaw installation part 120. The first joint ball 246A and the second joint ball 246B are each coupled to both end portions of the connection rod 246 by bolts.

The upper ball head part 244 includes a first ball housing cap 244C of which a lower portion is opened to accommodate a first ball housing 244A in which a first joint ball 246A is seated and an edge of an upper end is provided with a flange 244B, a first ball housing cover 244F including a first tension washer 244D seated on the flange 244B and having a first joint ball bushing 244E supporting the first joint ball 246A and installed in the first ball housing cover 244F, and an upper fixing bracket 244G coupled to an upper surface of the first ball housing cover 244F and having an upper surface coupled to the pressurizing member 114. The first tension washer 244D is to elastically support the first ball housing cap 244C and the first ball housing cover 244F.

The first ball housing 244A is disposed between the first ball housing cap 244C and the first joint ball bushing 244E and formed of silicone having hardness of 45 to 50 to elastically support the first ball housing cap 244C and the first joint ball bushing 244E using tension.

The lower ball head part 242 includes a second ball housing cap 242C of which an upper portion is opened to accommodate a second ball housing 242A in which a second joint ball 246B is seated and an edge of a lower end is provided with a flange 242B, a second ball housing cover 242F including a second tension washer 244D seated on the flange 242B, having a second joint ball bushing 242E supporting the second joint ball 246B and installed in the second ball housing cover 242F, and coupled to the upper surface of the upper jaw installation part 120.

Here, the second tension washer 242D is to elastically support the second ball housing cap 242C and the second ball housing cover 242F, the second ball housing 242A is disposed between the second ball housing cap 242C and the second joint ball bushing 242E and formed of silicone having hardness of 45 to 50 to elastically support the second ball housing cap 242C and the second joint ball bushing 242E using tension.

In the connection part 240, the lower end portion of the connection rod 246 is bendably and rotatably supported by the lower ball head part 242 within a range of 0 to 80° and the upper end portion of the connection rod 246 is bendably and rotatably supported by the upper ball head part 244 within a range of 0 to 80°, such that an ascending and descending operation of the pressurizing member 114 may be interlocked with the chewing motion of the upper jaw installation part 120 and the lower jaw installation part 130. That is, the upper jaw installation part 120 and the lower jaw installation part 130 are not vertically occluded, but flexibility may be given so that the chewing motion of the upper jaw installation part 120 and the lower jaw installation part 130 that is similar to that of the jaw joint of the human body may be made.

Only a portion of the functions of the probe device for analyzing physical properties of food, having a ball head linkage structure according to the third exemplary embodiment of the present invention that is distinguished from the second exemplary embodiment will be described.

As illustrated in FIGS. 17 and 18, in a state before the pressurizing member 114 is operated, when the pressurizing member 114 descends and pressurizes the connection member 240, the pressurizing force of the pressurizing member 114 is transferred to the upper jaw installation part 120 through the connection rod 246 of the connection part 240, thus the upper jaw installation part 120 rotates toward the lower jaw installation part 130 based on the connection shaft 166. In this case, when the pressurizing member 114 descends, the upper ball head part 244 and the upper end portion of the connection rod 246, and the lower ball head part 242 and the lower end portion of the connection rod 246 are freely bent within a predetermined range.

Because of such structure, connection between the pressurizing member 114 and the upper jaw installation part 120 is maintained even in a state in which a central axial line of the pressurizing member 114 and a central vertical line of the upper jaw installation part 120 are not matched with each other since the upper jaw installation part 120 is lifted upwardly based on the connection shaft 166 of the shaft coupling part 160, and when the pressurizing member 114 descends, the pressurizing force of the pressurizing member 114 is transferred to the upper jaw installation part 120 so that the upper jaw model 122 and the lower jaw model 132 are occluded with each other by a predetermined pressure thereby allowing the chewing motion to be performed.

Further, even when the pressurizing member 114 descends in a state in which the angle of the central block 152 of the base 150 is adjusted to incline the central block 152 forward so that the lower jaw model 132 is inclined forward, and the upper jaw installation part 120 is lifted upwardly in an inclined manner by the shaft coupling part 160, the respective tooth models 124 and 134 of the upper jaw model 122 and the lower jaw model 132 horizontally contact and are occluded with each other by the connection part 240 that may be multiply bent. That is, interlocking of the connection part 240 and the shaft coupling part 160 make the chewing motion of the upper jaw installation part 120 and the lower jaw installation part 130 similar to the chewing motion of the jaw joint of the human body, such that physical properties of food disposed between the respective tooth models 124 and 134 may be measured under a condition similar to that of the chewing motion of the human body.

Further, the first joint ball 246A and the second joint ball 246B of the connection part 240 rotate in the first ball housing 244A and the second ball housing 242A to support bending, thereby making the chewing motion of the upper jaw installation part 120 and the lower jaw installation part 130 by the ascending and descending operation of the pressurizing member 114 natural.

Although the specific exemplary embodiment of the present invention is explained and illustrated, but the present invention is not limited to the described exemplary embodiment. It is apparent to those skilled in the art that the exemplary embodiment of the present invention may be variously modified and changed without departing from the scope of the present invention. Therefore, such modifications and changes should be understood to fall with the concept and the scope of the present invention, and the modifications belong to the scope of the claims of the present invention.

INDUSTRIAL APPLICABILITY

According to the present invention, the probes having a teeth form corresponding to front teeth, canine teeth, and molars of the upper jaw and the lower jaw may be selectively attached and detached, such that physical properties of food may be more specifically and objectively measured as compared to the case of using the general probes according to the related art, and the vertical motion of the press device and the chewing motion of the upper jaw model and the lower jaw model are interlocked with each other by the connection part having a bearing structure or a ball head structure, such that the physical properties of food may be more accurately measured and objectively analyzed. In view of this fact, the present invention may be used for a related technique, and an apparatus to which the present invention is applied may also be marketed or available for business, and the present invention may be realistically and obviously carried out, and thus the present invention is industrially applicable.

The invention claimed is:

1. A probe device for analyzing physical properties of food, comprising:
   an upper jaw installation part including an upper jaw model in which respective upper jaw tooth models are installed, and coupled to a pressurizing member of a press device that vertically reciprocates;
   a lower jaw installation part including a lower jaw model in which lower jaw tooth models are installed, and coupled to the upper jaw installation part by a shaft coupling part so that the lower jaw model is occluded with the upper jaw model;
   a base on which the lower jaw installation part is installed and supported; and
   a connection part disposed between the pressurizing member and the upper jaw installation part and allowing the upper jaw installation part and the lower jaw installation part to perform a chewing motion by interlocking of the pressurizing member and the shaft coupling part,
   wherein the connection part includes a lower bearing part coupled to the upper jaw installation part; an upper bearing part coupled to the pressurizing member; and a connection rod having both ends each coupled to the upper bearing part and the lower bearing part so as to be freely bent within a predetermined angle range.

2. The probe device for analyzing physical properties of food of claim 1, wherein
   the lower bearing part includes a first bearing housing having a first bearing seating step on which a first bearing is seated and a first cover seating step on which a hollowed first bearing cover is seated that are formed therein, and coupled to an upper surface of the upper jaw installation part; and a first shaft joint coupled with a first coupling bolt that is inserted from a bottom surface of the first bearing housing in a state in which one end of the first shaft joint is inserted into the first bearing cover to be integrated with the first bearing housing while rotation of the first shaft joint itself is supported by the first bearing, and having a first joint formed at the other end of the first shaft joint and including a shaft hole for shaft-coupling the first joint to a lower end portion of the connection rod, and
   the upper bearing part includes a second bearing housing having a second bearing seating step on which a second bearing is seated and a second cover seating step on which a hollowed second bearing cover is seated that are formed therein, and coupled to a bottom surface of the pressurizing member; and a second shaft joint coupled with a second coupling bolt that is inserted from an upper surface of the second bearing housing in a state in which one end of the second shaft joint is inserted into the second bearing cover to be integrated with the second bearing housing while rotation of the second shaft joint itself is supported by the second bearing, and having a second joint formed at the other end of the second shaft joint and including a shaft hole for shaft-coupling the second joint to an upper end portion of the connection rod.

3. The probe device for analyzing physical properties of food of claim 2, wherein in both end portions of the connection rod, yoke parts to which the first joint and the second joint are inserted, respectively, and rotatably coupled using the shaft are formed, and joint bearings are each installed between the shaft hole and the shaft to support bending rotation of the first shaft joint and the second shaft joint.

4. The probe device for analyzing physical properties of food of claim 1, wherein the shaft coupling part includes a lower connection member having one end coupled to a rear surface of the lower jaw installation part; an upper connection member having one end coupled to a rear surface of the upper jaw installation part; and a connection shaft shaft-coupling the upper connection member and the lower connection member by penetrating through each of the other ends of the upper connection member and the lower connection member.

5. The probe device for analyzing physical properties of food of claim 1, wherein the base includes a central block on which the lower jaw installation part is seated and coupled; and side blocks each coupled to both sides of the central block to support the central block.

6. The probe device for analyzing physical properties of food of claim 5, wherein
   the base is provided with an angle adjusting unit for adjusting the central block to which the lower jaw installation part is coupled within a predetermined angle based on a horizontal line, and
   the angle adjusting unit includes a plurality of angle adjusting grooves formed at one side surface or both side surfaces of the central block to which the side blocks are coupled; and angle adjusting protrusions selectively inserted into the angle adjusting grooves and formed at the side block in a position corresponding to the angle adjusting grooves to fix an angle of the central block.

7. The probe device for analyzing physical properties of food of claim 6, wherein the angle adjusting grooves are radially disposed based on a fastening hole to which a coupling bolt for coupling the side block to the central block is fastened, and disposed each at both sides of the fastening hole, and the angle adjusting protrusions are each disposed at both sides thereof based on a bolt through hole through which the coupling bolt penetrates.

8. The probe device for analyzing physical properties of food of claim 5, wherein in the side blocks, long holes for sliding the central block forward or backward when the pressurizing member is operated to make the connection part operate the upper jaw installation part so that the chewing motion of the upper jaw model and the lower jaw model is performed are each formed in a vertical direction, and long bolts for coupling the side blocks to a bottom plate of the probe device penetrate through the long holes to be installed.

9. The probe device for analyzing physical properties of food of claim 5, wherein in the side blocks, long holes for changing a position of the central block toward a front side or a rear side and fixing the changed position are each formed in a vertical direction, position determining grooves are successively formed in the long holes, and long bolts for coupling the side blocks to a bottom plate of the probe device penetrate through the long holes to be installed.

10. A probe device for analyzing physical properties of food, comprising:
    an upper jaw installation part including an upper jaw model in which respective upper jaw tooth models are installed, and coupled to a pressurizing member of a press device that vertically reciprocates;
    a lower jaw installation part including a lower jaw model in which lower jaw tooth models are installed, and coupled to the upper jaw installation part by a shaft coupling part so that the lower jaw model is occluded with the upper jaw model;
    a base on which the lower jaw installation part is installed and supported; and
    a connection part disposed between the pressurizing member and the upper jaw installation part and allowing the upper jaw installation part and the lower jaw installation part to perform a chewing motion by interlocking of the pressurizing member and the shaft coupling part,
    wherein the connection part includes
        a lower ball head part coupled to the upper jaw installation part;
        an upper ball head part coupled to the pressurizing member; and
        a connection rod having both ends each coupled to the upper ball head part and the lower ball head part so as to be freely bent within a predetermined angle range.

11. The probe device for analyzing physical properties of food of claim 10, wherein
    the connection rod has an upper end portion and a lower end portion to which a first joint ball and a second joint ball are each coupled,
    the upper ball head part includes a first ball housing cap of which a lower portion is opened to accommodate a first ball housing in which the first joint ball is seated and an edge of an upper end is provided with a flange; a first ball housing cover including a first tension washer seated on the flange and having a first joint ball bushing supporting the first joint ball and installed in the first ball housing cover; and an upper fixing bracket coupled to an upper surface of the first ball housing cover and having an upper surface coupled to the pressurizing member, and
    the lower ball head part includes a second ball housing cap of which an upper portion is opened to accommodate a second ball housing in which the second joint ball is seated and an edge of a lower end is provided with a flange; and a second ball housing cover including a second tension washer seated on the flange, having a second joint ball bushing supporting the second joint ball and installed in the second ball housing cover, and coupled to an upper surface of the upper jaw installation part.

12. The probe device for analyzing physical properties of food of claim 11, wherein
    the first ball housing is disposed between the first ball housing cap and the first joint ball bushing and elastically supports the first ball housing cap and the first joint ball bushing using tension, and
    the second ball housing is disposed between the second ball housing cap and the second joint ball bushing and elastically supports the second ball housing cap and the second joint ball bushing using tension.

13. The probe device for analyzing physical properties of food of claim 11, wherein the lower end portion of the connection rod is bendably and rotatably supported by the lower ball head part within a range of 0 degrees to 80 degrees and the upper end portion of the connection rod is bendably and rotatably supported by the upper ball head part within a range of 0 degrees to 80 degrees.

14. The probe device for analyzing physical properties of food of claim 10, wherein the shaft coupling part includes a lower connection member having one end coupled to a rear surface of the lower jaw installation part; an upper connection member having one end coupled to a rear surface of the upper jaw installation part; and a connection shaft shaft-coupling the upper connection member and the lower connection member by penetrating through each of the other ends of the upper connection member and the lower connection member.

15. The probe device for analyzing physical properties of food of claim 10, wherein the base includes a central block on which the lower jaw installation part is seated and coupled; and side blocks each coupled to both sides of the central block to support the central block.

16. The probe device for analyzing physical properties of food of claim 15, wherein
    the base is provided with an angle adjusting unit for adjusting the central block to which the lower jaw installation part is coupled within a predetermined angle based on a horizontal line, and
    the angle adjusting unit includes a plurality of angle adjusting grooves formed at one side surface or both side surfaces of the central block to which the side blocks are coupled; and angle adjusting protrusions selectively inserted into the angle adjusting grooves and formed at the side block in a position corresponding to the angle adjusting grooves to fix an angle of the central block.

17. The probe device for analyzing physical properties of food of claim 16, wherein the angle adjusting grooves are radially disposed based on a fastening hole to which a coupling bolt for coupling the side block to the central block is fastened, and disposed each at both sides of the fastening hole, and the angle adjusting protrusions are each disposed at both sides thereof based on a bolt through hole through which the coupling bolt penetrates.

18. The probe device for analyzing physical properties of food of claim 17, wherein the angle adjusting grooves are radially disposed at both sides of the fastening hole to form a fan shape.

19. The probe device for analyzing physical properties of food of claim 15, wherein in the side blocks, long holes for sliding the central block forward or backward when the pressurizing member is operated to make the connection part operate the upper jaw installation part so that the chewing motion of the upper jaw model and the lower jaw model is performed are each formed in a vertical direction, and long bolts for coupling the side blocks to a bottom plate of the probe device penetrate through the long holes to be installed.

20. The probe device for analyzing physical properties of food of claim 15, wherein in the side blocks, long holes for changing a position of the central block toward a front side or a rear side and fixing the changed position are each formed in a vertical direction, position determining grooves are successively formed in the long holes, and long bolts for coupling the side blocks to a bottom plate of the probe device penetrate through the long holes to be installed.

* * * * *